(12) United States Patent
Deckman et al.

(10) Patent No.: US 8,702,679 B2
(45) Date of Patent: Apr. 22, 2014

(54) CATHETER SYSTEMS AND METHODS FOR CROSSING VASCULAR OCCLUSIONS

(75) Inventors: Robert K. Deckman, Redwood City, CA (US); Erik Thai, Redwood City, CA (US); Amiel R. Aguilar, Redwood City, CA (US); Benjamin J. Clark, Redwood City, CA (US); Sergio Salinas, Redwood City, CA (US); Daniel E. Francis, Redwood City, CA (US); Kurt D. Sparks, Redwood City, CA (US)

(73) Assignee: Cordis Corporation

( * ) Notice: Subject to any disclaimer, the term of this patent is extended or adjusted under 35 U.S.C. 154(b) by 1639 days.

(21) Appl. No.: 10/865,231

(22) Filed: Jun. 10, 2004

(65) Prior Publication Data
US 2005/0021002 A1    Jan. 27, 2005

Related U.S. Application Data

(60) Provisional application No. 60/477,628, filed on Jun. 10, 2003, provisional application No. 60/478,404, filed on Jun. 13, 2003.

(51) Int. Cl.
*A61M 25/00* (2006.01)

(52) U.S. Cl.
USPC .......................................................... 604/523

(58) Field of Classification Search
USPC .................................................. 604/527, 107
See application file for complete search history.

(56) References Cited

U.S. PATENT DOCUMENTS

| | | |
|---|---|---|
| 728,175 A | 5/1903 | Otto |
| 765,879 A | 7/1904 | Campbell |
| 832,201 A | 10/1906 | Kistler |
| 1,127,948 A | 5/1915 | Wappler |
| 1,267,066 A | 5/1918 | Flack |
| 2,621,651 A | 12/1952 | Wallace |
| 2,854,983 A | 10/1958 | Baskin |
| 3,485,234 A | 12/1969 | Stevens |
| 3,640,270 A | 2/1972 | Hoffmann |
| 3,667,474 A | 6/1972 | Lapkin et al. |

(Continued)

FOREIGN PATENT DOCUMENTS

| | | | |
|---|---|---|---|
| DE | 2945237 A1 | 5/1981 | |
| DE | 4429117 A1 | 2/1996 | |

(Continued)

OTHER PUBLICATIONS

U.S. Appl. No. 08/645,381, filed May 13, 1996 (Abandoned), Dinh, et al.

(Continued)

*Primary Examiner* — Jason Flick
*Assistant Examiner* — Diva K Chander

(57) ABSTRACT

Interventional catheter-based systems and methods are described herein for use in generating an initial pathway through vascular occlusions. The catheter systems generally include two elements. A first element is a Blunt Dissection Catheter including a manually actuated assembly located at the distal tip of the Blunt Dissection Catheter that performs blunt dissection in the vascular occlusion to produce a dissection track, or small pathway through the occlusion. The second element is a Sheath Catheter that serves as a conduit within which the Blunt Dissection Catheter is freely advanced, retracted and rotated. The first and second elements are used in some combination to cross vascular occlusions in both the coronary and peripheral vasculature.

3 Claims, 20 Drawing Sheets

(56) References Cited

U.S. PATENT DOCUMENTS

| | | |
|---|---|---|
| 4,043,323 A | 8/1977 | Komiya |
| 4,355,643 A | 10/1982 | Laughlin et al. |
| 4,541,433 A | 9/1985 | Baudino |
| 4,572,186 A | 2/1986 | Gould et al. |
| 4,585,000 A | 4/1986 | Hershenson |
| RE32,158 E | 5/1986 | Vukovic |
| 4,630,609 A | 12/1986 | Chin |
| 4,636,346 A | 1/1987 | Gold et al. |
| 4,648,402 A | 3/1987 | Santos |
| 4,669,467 A | 6/1987 | Willett et al. |
| 4,681,110 A | 7/1987 | Wiktor |
| 4,698,057 A | 10/1987 | Joishy |
| 4,723,549 A | 2/1988 | Wholey et al. |
| 4,737,142 A | 4/1988 | Heckele |
| 4,787,388 A | 11/1988 | Hofmann |
| 4,794,928 A | 1/1989 | Kletschka |
| 4,848,336 A | 7/1989 | Fox et al. |
| 4,862,874 A | 9/1989 | Kellner |
| 4,919,112 A | 4/1990 | Siegmund |
| 4,935,017 A | 6/1990 | Sylvanowicz |
| 5,001,556 A | 3/1991 | Nakamura et al. |
| 5,002,041 A | 3/1991 | Chikama |
| 5,011,488 A | 4/1991 | Ginsburg |
| 5,019,040 A | 5/1991 | Itaoka et al. |
| 5,030,201 A | 7/1991 | Palestrant |
| 5,034,001 A | 7/1991 | Garrison et al. |
| 5,061,254 A | 10/1991 | Karakelle et al. |
| 5,089,006 A | 2/1992 | Stiles |
| 5,092,839 A | 3/1992 | Kipperman |
| 5,098,381 A | 3/1992 | Schneider |
| 5,099,850 A | 3/1992 | Matsui et al. |
| 5,100,425 A | 3/1992 | Fischell et al. |
| 5,102,390 A | 4/1992 | Crittenden et al. |
| 5,114,414 A | 5/1992 | Buchbinder |
| 5,120,323 A | 6/1992 | Shockey et al. |
| 5,156,594 A | 10/1992 | Keith |
| 5,179,961 A | 1/1993 | Littleford et al. |
| 5,180,368 A | 1/1993 | Garrison |
| 5,192,290 A | 3/1993 | Hilal |
| 5,193,546 A | 3/1993 | Shaknovich |
| 5,197,971 A | 3/1993 | Bonutti |
| 5,209,729 A | 5/1993 | Hofmann et al. |
| 5,211,654 A | 5/1993 | Kaltenbach |
| 5,217,484 A | 6/1993 | Marks |
| 5,263,959 A | 11/1993 | Fischell |
| 5,263,963 A | 11/1993 | Garrison et al. |
| 5,263,967 A | 11/1993 | Lyons, III et al. |
| 5,279,565 A | 1/1994 | Klein et al. |
| 5,279,656 A | 1/1994 | Kenyon et al. |
| 5,282,817 A | 2/1994 | Hoogeboom et al. |
| 5,304,199 A | 4/1994 | Myers |
| 5,321,501 A | 6/1994 | Swanson et al. |
| 5,334,210 A | 8/1994 | Gianturco |
| 5,336,252 A | 8/1994 | Cohen |
| 5,350,377 A | 9/1994 | Winston et al. |
| 5,351,678 A | 10/1994 | Clayton et al. |
| 5,383,467 A | 1/1995 | Auer et al. |
| 5,409,453 A | 4/1995 | Lundquist et al. |
| 5,415,636 A | 5/1995 | Forman |
| 5,423,846 A | 6/1995 | Fischell |
| 5,423,885 A | 6/1995 | Williams |
| 5,439,000 A | 8/1995 | Gunderson et al. |
| 5,456,667 A | 10/1995 | Ham et al. |
| 5,459,570 A | 10/1995 | Swanson et al. |
| 5,484,412 A | 1/1996 | Pierpont |
| 5,486,170 A | 1/1996 | Winston et al. |
| 5,486,193 A | 1/1996 | Bourne et al. |
| 5,490,859 A | 2/1996 | Mische et al. |
| 5,493,000 A | 2/1996 | Aharoni |
| 5,499,995 A | 3/1996 | Teirstein |
| 5,501,694 A | 3/1996 | Ressemann et al. |
| 5,507,295 A | 4/1996 | Skidmore |
| 5,507,296 A | 4/1996 | Bales et al. |
| 5,511,559 A | 4/1996 | Vance |
| 5,522,819 A | 6/1996 | Graves et al. |
| 5,538,513 A | 7/1996 | Okajima |
| 5,540,707 A | 7/1996 | Ressemann et al. |
| 5,556,408 A | 9/1996 | Farhat |
| 5,569,298 A | 10/1996 | Schnell |
| 5,573,531 A | 11/1996 | Gregory |
| 5,599,306 A | 2/1997 | Klein et al. |
| 5,613,947 A | 3/1997 | Chin |
| 5,618,300 A | 4/1997 | Marin et al. |
| 5,626,599 A | 5/1997 | Bourne et al. |
| 5,626,607 A | 5/1997 | Malecki et al. |
| 5,649,941 A | 7/1997 | Lary |
| 5,653,684 A | 8/1997 | Laptewicz et al. |
| 5,662,671 A | 9/1997 | Barbut et al. |
| 5,680,873 A | 10/1997 | Berg et al. |
| 5,683,451 A | 11/1997 | Lenker et al. |
| 5,688,234 A | 11/1997 | Frisbie |
| 5,695,515 A | 12/1997 | Orejola |
| 5,707,390 A | 1/1998 | Bonutti |
| 5,713,907 A | 2/1998 | Hogendijk et al. |
| 5,752,973 A | 5/1998 | Kieturakis |
| 5,762,613 A | 6/1998 | Sutton et al. |
| 5,766,151 A | 6/1998 | Valley et al. |
| 5,800,450 A | 9/1998 | Lary et al. |
| 5,816,923 A | 10/1998 | Milo et al. |
| 5,876,385 A | 3/1999 | Ikari et al. |
| 5,891,114 A | 4/1999 | Chien et al. |
| 5,893,875 A | 4/1999 | O'Connor |
| 5,911,715 A | 6/1999 | Berg et al. |
| 5,913,870 A | 6/1999 | DeFonzo et al. |
| 5,935,122 A * | 8/1999 | Fourkas et al. ............... 604/523 |
| 5,964,779 A | 10/1999 | Mayenberger |
| 5,968,064 A | 10/1999 | Selmon et al. |
| 5,978,714 A | 11/1999 | Zadini et al. |
| 6,010,449 A | 1/2000 | Selmon et al. |
| 6,015,423 A | 1/2000 | Andrese |
| 6,042,578 A | 3/2000 | Dinh et al. |
| 6,059,769 A | 5/2000 | Lunn et al. |
| 6,120,516 A | 9/2000 | Selmon et al. |
| 6,165,163 A * | 12/2000 | Chien et al. ................... 604/523 |
| 6,217,549 B1 * | 4/2001 | Selmon et al. ................ 604/106 |
| 6,228,073 B1 | 5/2001 | Noone |
| 6,251,104 B1 | 6/2001 | Kesten et al. |
| 6,325,790 B1 | 12/2001 | Trotta |
| 6,375,665 B1 | 4/2002 | Nash et al. |
| 6,375,774 B1 | 4/2002 | Lunn et al. |
| 6,398,798 B2 | 6/2002 | Selmon et al. |
| 6,436,119 B1 | 8/2002 | Erb et al. |
| 6,464,684 B1 * | 10/2002 | Galdonik ....................... 604/527 |
| 6,503,353 B1 | 1/2003 | Peterson et al. |
| 6,508,825 B1 | 1/2003 | Selmon et al. |
| 6,520,973 B1 | 2/2003 | McGarry |
| 6,558,349 B1 | 5/2003 | Kirkman |
| 6,599,304 B1 | 7/2003 | Selmon et al. |
| 6,638,247 B1 | 10/2003 | Selmon et al. |
| 6,800,085 B2 | 10/2004 | Selmon et al. |
| 2002/0107526 A1 * | 8/2002 | Greenberg et al. ........... 606/108 |
| 2002/0188278 A1 | 12/2002 | Tockman et al. |
| 2004/0077999 A1 | 4/2004 | Selmon et al. |
| 2004/0087933 A1 * | 5/2004 | Lee et al. ...................... 604/532 |
| 2004/0153049 A1 * | 8/2004 | Hewitt et al. .................. 604/527 |

FOREIGN PATENT DOCUMENTS

| | | |
|---|---|---|
| EP | 0268228 A2 | 5/1988 |
| EP | 0277366 A1 * | 8/1988 |
| EP | 0303487 A2 | 2/1989 |
| EP | 0377269 A1 | 7/1990 |
| EP | 0439932 A1 | 8/1991 |
| EP | 0521595 A2 | 1/1993 |
| EP | 0643980 | 9/1994 |
| EP | 0439932 B1 | 11/1994 |
| EP | 0268228 | 1/1996 |
| EP | 0723786 A1 | 7/1996 |
| EP | 1635900 B1 | 4/2009 |
| FR | 1585065 | 1/1970 |
| JP | A1998238876 | 10/1988 |
| JP | A1991-082473 | 4/1991 |
| JP | 1992-502412 A | 5/1992 |
| JP | A1992-341275 | 11/1992 |

(56) References Cited

FOREIGN PATENT DOCUMENTS

| | | |
|---|---|---|
| JP | A2004-000221 | 1/1994 |
| JP | A1996-299287 | 11/1996 |
| JP | 09-121333 | 2/1998 |
| JP | A1999500939 | 1/1999 |
| JP | 01-518325 | 4/1999 |
| JP | 00-140120 | 5/2000 |
| JP | A2000-506514 | 5/2000 |
| JP | 2001-178814 | 7/2001 |
| JP | A2001-515773 | 9/2001 |
| JP | A2001-520085 | 10/2001 |
| JP | 2001-521795 A | 11/2001 |
| JP | A2002-504400 | 2/2002 |
| JP | A2002-517263 | 6/2002 |
| JP | 2003-530168 A | 10/2003 |
| JP | A2008-538309 | 10/2008 |
| SU | 0134398 | 1/1960 |
| WO | 83/03188 | 9/1983 |
| WO | WO90/01345 | 2/1990 |
| WO | 91/02493 | 3/1991 |
| WO | 91/19528 | 12/1991 |
| WO | 92/08510 | 5/1992 |
| WO | 93/18818 | 9/1993 |
| WO | 95/19143 | 7/1995 |
| WO | 96/01590 | 1/1996 |
| WO | 96/11636 | 4/1996 |
| WO | WO 96/11636 A1 | 4/1996 |
| WO | WO96/26758 | 9/1996 |
| WO | WO97/27888 | 8/1997 |
| WO | 98/40015 | 9/1998 |
| WO | WO99/12609 | 9/1998 |
| WO | WO99/07431 A1 | 2/1999 |
| WO | WO99/43366 | 2/1999 |
| WO | WO99/20326 | 4/1999 |
| WO | 99/23957 | 5/1999 |
| WO | WO99/22797 | 5/1999 |
| WO | 99/40963 | 8/1999 |
| WO | 00/20064 | 4/2000 |
| WO | WO01/07101 | 2/2001 |
| WO | WO01/76682 A1 | 10/2001 |
| WO | WO 02/32330 A2 | 4/2002 |
| WO | WO2006/110830 | 10/2006 |

OTHER PUBLICATIONS

International Search Report for corresponding Patent Application No. PCT/US2004/018538 mailed Feb. 1, 2005.
Mexican Search Report for corresponding Patent Application No. PA/a/2005/013448 mailed Jul. 27, 2010.
Chinese Search Report for corresponding Patent Application No. 200480019881.6 mailed Nov. 21, 2008.
Brief Communication from the European Patent Office dated Mar. 8, 2011 relating to European Patent Application No. 04776454.3-2320 (Opposition).
Product Brochure on "Rotablator, Rotational Angioplasty System", Boston Scientific Scimed, dated May 20002.
M. Fuji et al., "Development of Adhesive Technology for PTFE on Metal Substances—Surface Modification of PTFE by Plasma Etching Treatment", vol. 99, pp. 78-84 (Jul. 2002).
Product Brochure on "Rotablator", Boston Scientific Scimed, dated May 2002.
Extract from "thefreedictionary.com" for the term "dissection", http://medical-dictionary.thefreedictionary.com/p/blunt dissection, 2007.

* cited by examiner

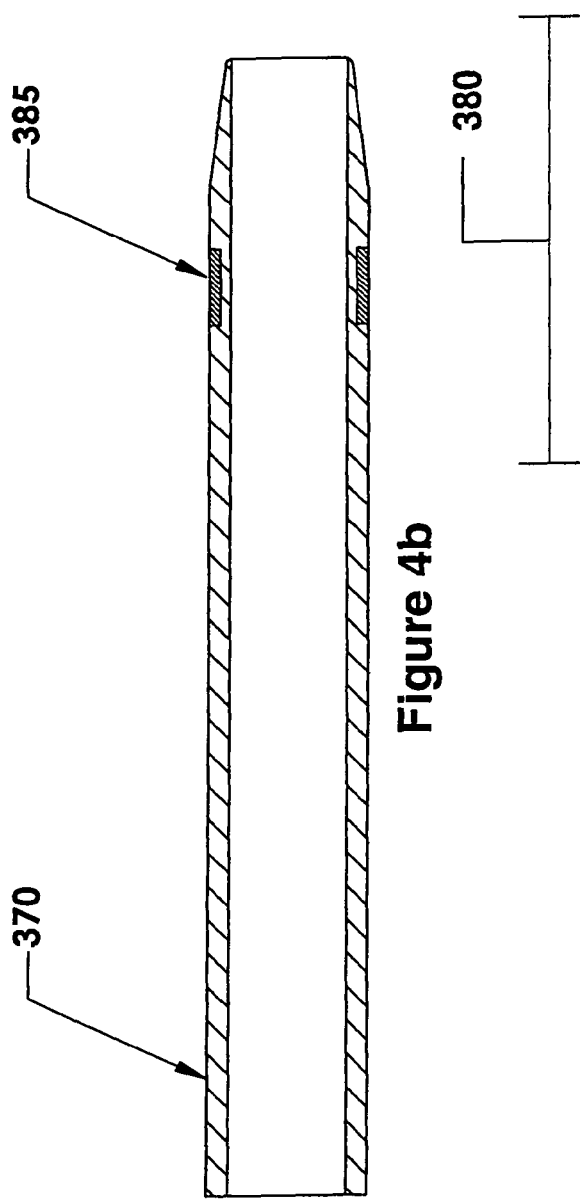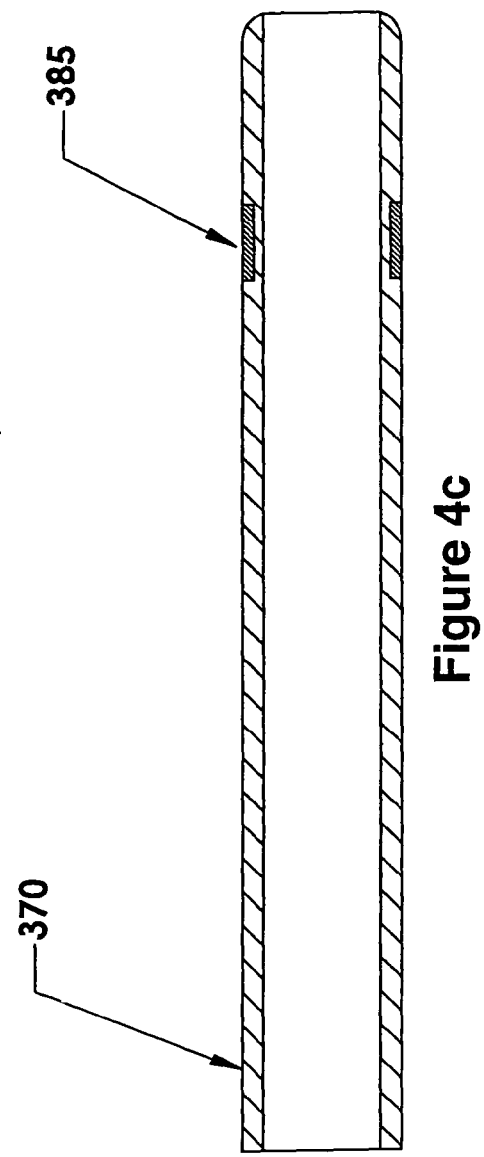

CATHETER SYSTEMS AND METHODS FOR CROSSING VASCULAR OCCLUSIONS

RELATED APPLICATIONS

This application claims priority from U.S. patent application No. 60/477,628, filed Jun. 10, 2003, and No. 60/478,404, filed Jun. 13, 2003.

This application is related to U.S. patent application Ser. No. 09/835,043, filed April 13, 2001, Ser. No. 10/074,546, filed Feb. 12, 2002, and Ser. No. 10/647,904, filed Aug. 25, 2003. This application is also related to U.S. patent application Ser. Nos. 08/775, 264, filed Feb. 28, 1997, now U.S. Pat. No. 5,968,064, Ser. No. 09/149,874, filed Sep. 8, 1998, now U.S. Pat. No. 6,508,825, Ser. No. 09/443,924, filed Nov. 19, 1999, now U.S. Pat. No. 6,599,304, and Ser. No. 09/538,441, filed Oct. 28, 2003, now U.S. Pat. No. 6,638,247.

FIELD OF THE INVENTION

The systems and methods described herein relate to medical devices and, more specifically, to catheter-based systems for treating occlusions within blood vessels of the human or mammalian body.

BACKGROUND

Vascular occlusions are blockages of the cardiovascular system (which includes both coronary and peripheral vessels) that significantly or completely block the flow of blood through the vessel. The progression of the disease state that causes vascular occlusions, generally referred to as atherosclerosis involves the gradual deposition of fatty, fibrous and/or calcific deposits along the interior wall of the vessel. This progression may occur slowly, sometimes taking a number of years. Vascular occlusions may be categorized as "functional" or as a Chronic Total Occlusion (CTO). The occlusions are functional, for example, when the vessel has developed significant stenosis that blocks the majority of blood flow, but a small finite pathway remains through the vessel. The occlusions are categorized as CTOs when the progression of the disease state has completely occluded the vessel and has stopped all flow of blood through the vessel at the point of the occlusion.

In arterial disease, often as the lumen of the native vessel begins to slowly close, the tissue served by this native vessel becomes ischemic and the body may respond by generating angiogenic factors that initiate the growth of new "collateral" vessels that originate proximal to the site of the occlusion and feed the tissue distal to the occlusion. These new vessels may help to stabilize the tissue's requirement for blood flow and oxygen during rest or nominal activity. These collateral vessels may occur in both the coronary and peripheral vasculature. However, often these new collateral vessels cannot sustain an adequate delivery of blood and oxygen to the tissue under more demanding situations such as exercise. For blockages in peripheral vessels such as in the legs, the patient may develop clinical symptoms such as claudication in the legs (pain while exercising), or in the case of coronary blockages the patient may develop shortness of breath or chest pain while exercising.

The physical treatment of vascular occlusions may involve interventional methods (for example, non-surgical, catheter based methods), or surgical methods. The intent of interventional treatment is to re-cannalize the occluded vessel by first generating an initial small pathway through the occlusion, and subsequently radially expanding the small pathway via balloon angioplasty to a diameter that is nominally equal to the original diameter of the vessel prior to its becoming occluded. The site may also be treated with athrectomy catheters and stents as well to facilitate the long term patency of the vessel.

Interventional treatment typically involves introducing a specialized wire, referred to as a guide wire, into the vessel that is proximal to the occlusion and advancing the guide wire using fluoroscopic means through the occlusion and into the vessel that is distal to the occlusion. This fundamental technique may be practiced in both coronary (heart) vessels and peripheral (for example, iliac, superficial femoral, sub-clavian) vessels. Once the guide wire is delivered through the occlusion and into the vessel lumen distal to the occlusion, a balloon catheter may be delivered over the guide wire to perform balloon angioplasty at the site of the occlusion.

However, conventional guide wires are not designed for generating pathways through total occlusions. Rather they are designed with very flexible distal terminations to allow them to typically navigate through non-occluded but stenosed vessels, for the purpose of the subsequently delivery of a balloon catheter to perform angioplasty at the site of the stenosed artery. The design of a guide wire capable of generating a pathway through a total occlusion is a challenging task, whereas the guide wire must be robust enough to pass through the occlusive material, but also be friendly enough so as not to perforate through the vessel wall, should the guide wire not take a direct path through the occlusion. However, the divergence of the guide wires pathway through the occlusion is a clear possibility, since the composition of a total occlusion can be very non-homogeneous, leading to the guide wires deflection off of fibrous or hard calcific deposits, leading to its potential advancement through the vessel wall, which is clearly undesirable.

Interventional methods to treat vascular total occlusions can be challenging and problematic, and present high risk factors, as described above. As such, patients presenting with vascular total occlusions are frequently referred directly to the surgical method of treatment. Alternatively, patients are frequently referred to surgical methods following the failure of an interventional attempt. While the surgical approach is clearly more traumatic to the patient, the actual mechanics of the procedure are more straightforward the procedure is generally accepted as having fewer complications.

In the surgical approach, an external conduit is used to bypass the occlusion, wherein one end of the conduit is attached to the vessel proximal to the occlusion, and the other end of the conduit is attached to the vessel distal to the occlusion. In this way, the flow of blood is re-routed around the occlusion. The conduit may be an explanted section of artery or vein, or may be a man-made conduit, typically fabricated of a Dacron composition.

The surgical approach however is also not without complications. Whereas the surgical approach generally results in favorable clinical outcomes, it is very invasive as compared to the interventional approach and subsequently leads to a much greater recovery period for the patient. Consequently, in reviewing the surgical and interventional approaches to treating chronic total occlusions, it is evident that a non-surgical approach would be desirable, and an improved interventional treatment would be further desirable that could increase success rates and lessen the complications associated with present interventional procedures.

BRIEF DESCRIPTION OF THE DRAWINGS

FIG. 4b is a longitudinal cross-section of an Introducer Catheter distal segment in a tapered configuration and including a fluoroscopic marker band, under an embodiment.

FIG. 4c is a longitudinal cross-section of an Introducer Catheter distal segment in a rounded configuration and including a fluoroscopic marker band, under an embodiment.

In the drawings, the same reference numbers identify identical or substantially similar elements or acts.

DETAILED DESCRIPTION

Figure 1:
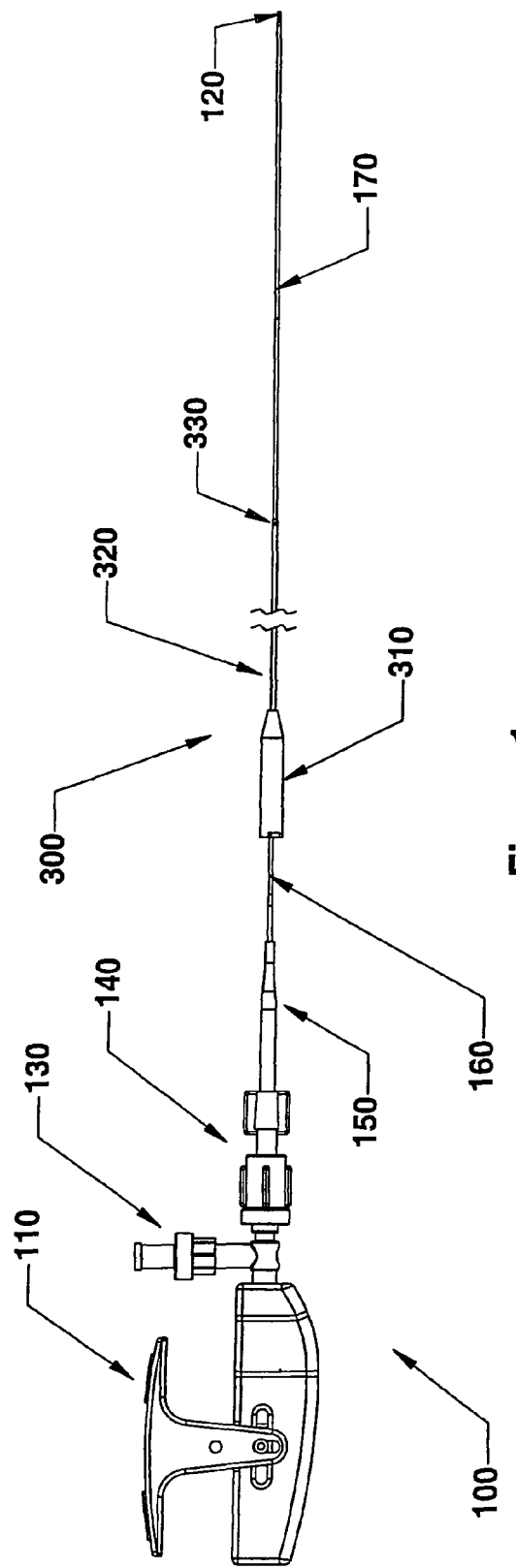
FIG. 1 is a catheter system including a Blunt Dissection Catheter and Sheath Catheter, under an embodiment.

Interventional catheter-based systems and methods are described herein for use in generating an initial pathway through a vascular total occlusion. It should be noted that the system described herein does not perform a therapeutic function in that the initial pathway generated by the catheter system through the vascular occlusion is not intended to restore functional patency or blood flow to the vessel. Rather, after having generated the pathway through the occlusion, the catheter system may be extracted in whole or in part from the vessel. The generated pathway is subsequently used for passage of a conventional guide wire, with the guide wire then serving a conventional function to deliver therapeutic devices such as balloon catheters or stents for performing conventional angioplasty or stenting to the previously occluded vascular site. Thus the generation of this initial pathway is only to facilitate the subsequent placement of a conventional guide wire, and without the placement of the guide wire across the occlusion, further therapeutic procedures are not possible. The system described herein is applicable for use in any vasculature of the body.

In the following description, numerous specific details are introduced to provide a thorough understanding of, and enabling description for, embodiments of the catheter systems and methods. One skilled in the relevant art, however, will recognize that these embodiments can be practiced without one or more of the specific details, or with other components, systems, etc. In other instances, well-known structures or operations are not shown, or are not described in detail, to avoid obscuring aspects of the disclosed embodiments.

The catheter system described herein generally includes two elements. The first element is a Blunt Dissection Catheter including a remotely, manually actuated assembly located at the distal tip of the catheter that performs blunt dissection in the vascular occlusion to produce a dissection track, or small pathway through the occlusion. The second element is a Sheath Catheter that serves as a conduit within which the Blunt Dissection Catheter may be freely advanced, retracted or rotated. These elements are used in conjunction with each other to cross total vascular occlusions in both the coronary and peripheral vasculature. Descriptions of each element follow below.

The Blunt Dissection Catheter of an embodiment includes a catheter shaft that is distally terminated with a working element (also referred to as a distal actuation assembly or distal assembly) including of one or more longitudinally arranged, atraumatic, blunt spreading member(s), each spreading member having a free distal end configured to rotate about a proximal end that is hinged to a base of the assembly, the base being non-moveable and attached to the distal end of the catheter shaft. The spreading members are remotely actuated via the catheters proximal handle, and move between a normally closed position wherein the catheter may be advanced, retracted and properly positioned within the vessel, and an open, actuated position during which the blunt dissection process occurs. In the closed position, the free distal end of the spreading member(s) is rotated towards the central axis of the catheter shaft, and the spreading member(s) form a smooth, blunt, bullet-shaped configuration at the end of the catheter shaft. In the open configuration, the distal end of the spreading member(s) is rotated about the proximal hinged attachment to the base and the spreading member(s) moves through an arc and laterally away from the central axis of the catheter.

An actuation element is disposed within the catheter shaft of an embodiment, the distal end of the actuation element being in contact with the hinged spreading member(s), and the proximal end of the actuation element coupled to the proximally actuated handle mechanism. The handle mechanism is operable by the physician, for example. Actuation of the handle imparts an axial force to the actuation element, which in turn imparts an opening force to the spreading members of the working element. The working element responds wherein the one or more atraumatic, blunt spreading member(s) rotate about their proximal hinge attachment to the base, and the free distal end of the spreading member travels through an arc and laterally away from the central axis of the catheter.

When positioned against a vascular occlusion, the lateral movement of the distal spreading member imparts a force to the occlusive vascular tissue to locally disrupt the occlusion and produce a small dissection track immediately distal to the working element. The catheter may then be advanced distally into this small dissection track, and the process repeated, each time producing another small dissection track immediately distal to the catheter working element, into which the catheter moves. The process continues until the catheter has advanced through the vascular occlusion, and exits into the true lumen of the vessel that is distal to the occlusion. Blunt dissection catheters usable as the first element of the catheter system are described in the Related Applications.

The second element of the catheter system is the Sheath Catheter, which is designed as a complimentary device within which the Blunt Dissection Catheter operates. The Sheath Catheter of an embodiment is a low profile conduit, and includes a single lumen, thin walled catheter shaft terminating distally in an atraumatic distal port and terminating proximally in a single port hub. The wall thickness of the Sheath Catheter is desired to be as thin as physically possible, and the inner diameter of the Sheath Catheters single lumen is designed to provide a high tolerance fit to the outer diameter of the Blunt Dissection Catheter. These two attributes afford the least overall profile to the composite catheter system, which facilitates the advancement of the catheter system through the vasculature, and is especially critical to facilitate the movement of the system through heavily diseased areas of the vessel.

The outer surface of the Blunt Dissection Catheter and the inner surface of the Sheath Catheter are lubricious to each other because of the minimized annular space between the surfaces; this facilitates the free rotational and axial movement of the Blunt Dissection Catheter within the Sheath Catheter. This lubricity is achieved by including a lubricious material such as high density polyethylene (HDPE), low density polyethylene (LDPE) or polytetrafluoroethelyene (PTFE) in materials of the inner surface of the Sheath Catheter. The outer surface of the Blunt Dissection Catheter shaft can also be designed with similar materials, or other polymers such as nylons or polyurethanes, and a hydrophilic coating may be applied to the surface of the catheter to increase lubricity.

The annular space between the outer diameter of the Blunt Dissection Catheter and the inner diameter of the Sheath Catheter of an embodiment is on the order of approximately 0.001 inches, but is not so limited. Wall thickness of the Sheath Catheter of an embodiment ranges from approximately 0.003 to 0.010 inches, but is not so limited. Nominal wall thickness is approximately 0.005 inches. A small annular space between the Blunt Dissection Catheter and the Sheath Catheter, in combination with a minimized wall thickness of the Sheath Catheter, but especially at the terminal end, minimizes the overall exposed leading edge of the Sheath Catheter as it translates over the Blunt Dissection Catheter during advancement within the vascular system.

Procedurally, the catheter system including the Blunt Dissection Catheter and Sheath Catheter is advanced within a vessel until the working element of the Blunt Dissection Catheter is brought into intimate contact with the vascular occlusion. In this process, the Blunt Dissection Catheter remains in an advanced position just beyond the distal end of the Sheath Catheter, typically approximately 1 to 15 centimeters (cm). In order to perform the blunt dissection process, the working element of the Blunt Dissection Catheter is engaged with sufficient force into the vascular occlusion using axial force input into the Blunt Dissection Catheter by the physician via the proximal handle.

The translation of this force from the handle to the working element is facilitated by two factors. The first factor to facilitate the translation of axial force is the physical support offered by the Sheath Catheter. On its own the Blunt Dissection Catheter is designed to have more flexibility to be able to easily navigate through the vascular system. However, this design consideration also tends to reduce the overall amount of inherent "push" the catheter can develop on its own. Thus, the physical support offered by the Sheath Catheter increases the overall "pushability" of the system. The second factor to facilitate the translation of axial force is the lubricity between the inner surface of the Sheath Catheter and the outer surface of the Blunt Dissection Catheter. These two factors maximize the translation of force delivered to the working element of the Blunt Dissection Catheter, and facilitate the overall blunt dissection process.

Maximizing the translation of axial force delivered to the Blunt Dissection Catheter working element is the first fundamental function provided by the Sheath Catheter. Greater translation of axial force input by the physician allows the working element to better engage the total occlusion and facilitates the blunt dissection process. As the Blunt Dissection Catheter is incrementally advanced through the vascular occlusion, the Sheath Catheter may also be advanced forward as appropriate to the procedure and the patient in order to provide the proper support to the Blunt Dissection Catheter. Typically, the distal end of the Sheath Catheter is maintained at a distance of from approximately 1 to 5 cm proximal to the Blunt Dissection Catheter to provide proper support.

As the Blunt Dissection Catheter progresses further into material of the vascular occlusion, the Sheath Catheter can also be incrementally advanced forward. As this proceeds, the Sheath Catheter will reach the proximal end of the occlusion, where the dissection track begins. Up to this point, the distal end of the Sheath Catheter may have been advancing within a diffusely diseased portion of the vessel. However, upon now reaching the proximal end of the vascular occlusion, where the dissection track begins, the working diameter of the vessel lumen will have been reduced down to the size of the dissection track produced by the Blunt Dissection Catheter. The ability to now advance the Sheath Catheter distally to follow the Blunt Dissection Catheter into the occlusion now becomes dependent on the high tolerance fit between the Sheath Catheter and the Blunt Dissection Catheter, and the low profile of the leading edge of the Sheath Catheter. A very low profile leading edge of the Sheath Catheter of an embodiment allows the Sheath Catheter to follow over the Blunt Dissection Catheter into the dissection track.

As both the Blunt Dissection Catheter and Sheath Catheter are incrementally advanced through the vascular occlusion, the Blunt Dissection Catheter eventually exits the vascular occlusion and enters the true lumen of the vessel that is distal to the occlusion. At this point during the procedure, the position of the Blunt Dissection Catheter is maintained, and the Sheath Catheter can be further advanced distally over the Blunt Dissection Catheter until the Sheath Catheter has also exited the occlusion, and entered the true lumen of the vessel that is distal to the occlusion. The Blunt Dissection Catheter may then be extracted from the vessel and the body completely, leaving the Sheath Catheter in place across the vascular occlusion.

The placement of the Sheath Catheter across the occlusion now serves as a convenient conduit through which a conventional guide wire may be advanced into the true lumen of the vessel that is distal to the occlusion. This is the second fundamental function afforded by the Sheath Catheter. Having now placed the guide wire across the vascular occlusion, its position is maintained and the Sheath Catheter may be extracted from the vessel and the body. The guide wire is thus left in place to facilitate the delivery of therapeutic devices such as balloon catheters or stents to perform angioplasty or stenting to treat the previously occluded vascular site.

FIG. 1 is a catheter system including a Blunt Dissection Catheter 100 and Sheath Catheter 300, under an embodiment. The Blunt Dissection Catheter 100 and Sheath Catheter 300 are shown as an integral system with the Blunt Dissection Catheter 100 positioned within the Sheath Catheter 300. The Blunt Dissection Catheter 100 has a longer working length than the overall physical length of the Sheath Catheter 300. Working length is generally defined as the usable length of the catheter shaft that may be advanced into another device, and in this case the Blunt Dissection Catheter 100 is advanced into the Sheath Catheter 300. Working length is measured from the tip of a catheter to the proximal most point on the catheter shaft. In the Blunt Dissection Catheter 100, the working length extends from the working element 120 to the distal end of the strain relief 150 that interfaces the catheter shaft 160 to the handle 110. The Blunt Dissection Catheter shaft 160 can be advanced into the Sheath Catheter 300 until the Blunt Dissection Catheter strain relief 150 butts against the Sheath Catheters proximal hub 310. When the Blunt Dissection Catheter 100 has been fully advanced into the Sheath Catheter 300, a distal segment of the Blunt Dissection Catheter 170 extends from the distal tip 330 of the Sheath Catheter 300. This length may typically vary from approximately 1 cm to 15 cm, but is not so limited. The nominal extended length is approximately 10 cm, but is not so limited.

The working length of the Blunt Dissection Catheter 100, and the corresponding overall length of the Sheath Catheter 300 depends on the area of the body in which the system is used, the entry point into the body, and the pathway the catheter takes through the body to the occlusion. Commonly treated sites in the peripheral vasculature are in the two main vessel branches that bifurcate from the distal aorta, each supplying blood to the trunk area and one of the legs. Each iliac artery tapers into the femoral artery through the groin and upper thigh area, and further tapers into the popliteal artery in the area of the knee.

The typical catheter system entry point into the peripheral vasculature is through the femoral artery location in either groin. From this entry site, the catheter system may be advanced in one of two directions. If the occlusion is in the artery distal to the entry site, the catheter system is advanced distally and in the direction of blood flow until the occlusion is reached. This approach is commonly referred to as "ipsa-lateral", meaning the entry site and the treatment site are located in the same vascular branch on the "same side" of the aortic bifurcation. Alternatively, if the occlusion is located in the vascular branch opposite of the entry site, the catheter may utilize the same entry site, but is first advanced against the flow of blood to reach the terminal end of the aorta, and then directed into the opposite iliac arterial branch. The catheter may then be advanced distally to reach the occlusion. This approach is commonly referred to as "contra-lateral" since the vascular occlusion site and the entry site are in opposite legs of the aortic bifurcation.

Nominal working length required for the Blunt Dissection Catheter 100 in ipsa-lateral applications ranges from approximately 40 cm to 100 cm, but is not so limited. A typical working length of the Blunt Dissection Catheter 100 for ipsa-lateral applications is approximately 80 cm. Accordingly, the overall length of the Sheath Catheter 300 is nominally approximately 10 cm shorter than the working length of the Blunt Dissection Catheter 130, and may range from approximately 30 cm to 90 cm, but is not so limited.

For contra-lateral applications, the Blunt Dissection Catheter 100 catheter must first reach the terminal aorta via the iliac artery proximal to the entry site before being directed distally into the opposing iliac artery. For a vascular occlusion, in the iliac artery opposite of the entry site, a working length of only approximately 60 cm may be used. However, if the vascular occlusion is in the Superficial Femoral Artery (SFA) or in the popliteal artery, the working length may reach approximately 140 cm, or possibly 160 cm. A practical working length range of the Blunt Dissection Catheter 100 for contra-lateral applications is approximately 60 cm to 140 cm, but is not necessarily so limited. Accordingly, the overall length of the Sheath Catheter 300 may range from 50 cm to 130 cm, but is not so limited. All catheter dimensions provided above and elsewhere herein are presented as examples only and may be different according to vascular entry site, location of the vascular occlusion, and medical procedure.

For access to the coronary vasculature, the entry site may be the same as for the peripheral vasculture, namely through the femoral artery in the groin. Minimum working length for the Blunt Dissection Catheter 100 of an embodiment is approximately 110 cm. The upper range is similar to that of the peripheral version, or approximately 140 cm. A typical overall range of length may be from approximately 110 cm to 140 cm, but is not so limited. Accordingly, the overall length of the Sheath Catheter 300 may range from approximately 100 cm to 130 cm, but is also not so limited.

The Blunt Dissection Catheter 100 is shown with proximal handle 110, flush port 130, rotating haemostasis valve 140, strain relief 150, proximal catheter shaft 160, distal catheter shaft 170, and working element 120. Actuation of the handle mechanism 110 communicates an opening and closing action to the catheters working element 120. Specifically, depression of the distal segment of the "T" handle 110 imparts proximal axial movement of the actuation element (not shown) within the catheter shaft 160/170, which in turn opens the spreading members 122 of the working element 120. Depression of the proximal segment of the "T" handle 110 imparts distal axial movement of the actuation element (not shown) within the catheter shaft 160/170, which in turn closes the spreading members 122 of the working element 120. The handle assembly 110 may be constructed of common machinable plastics such as polycarbonate or Delrin, but is not so limited.

The flush port 130 provides a pathway to inject saline into the interior of the catheter 100 to displace any air prior to insertion into the body. The rotating haemostasis valve 140 maintains a fluid-tight pathway between the interior of the catheter shaft 160/170 and the flush port 130, while allowing the catheter shaft 160/170 to be rotated as required by the physician during use.

The Sheath Catheter 300 includes the proximal hub 310, the shaft 320, and the distal termination 330. As stated previously, the overall length of the Sheath Catheter 300 is such that upon complete distal advancement of the Blunt Dissection Catheter 100 into the Sheath Catheter 300 approximately 10 cm of the Blunt Dissection Catheter 100 extends from the distal end of the Sheath Catheter 300, but is not so limited.

Figure 2A:
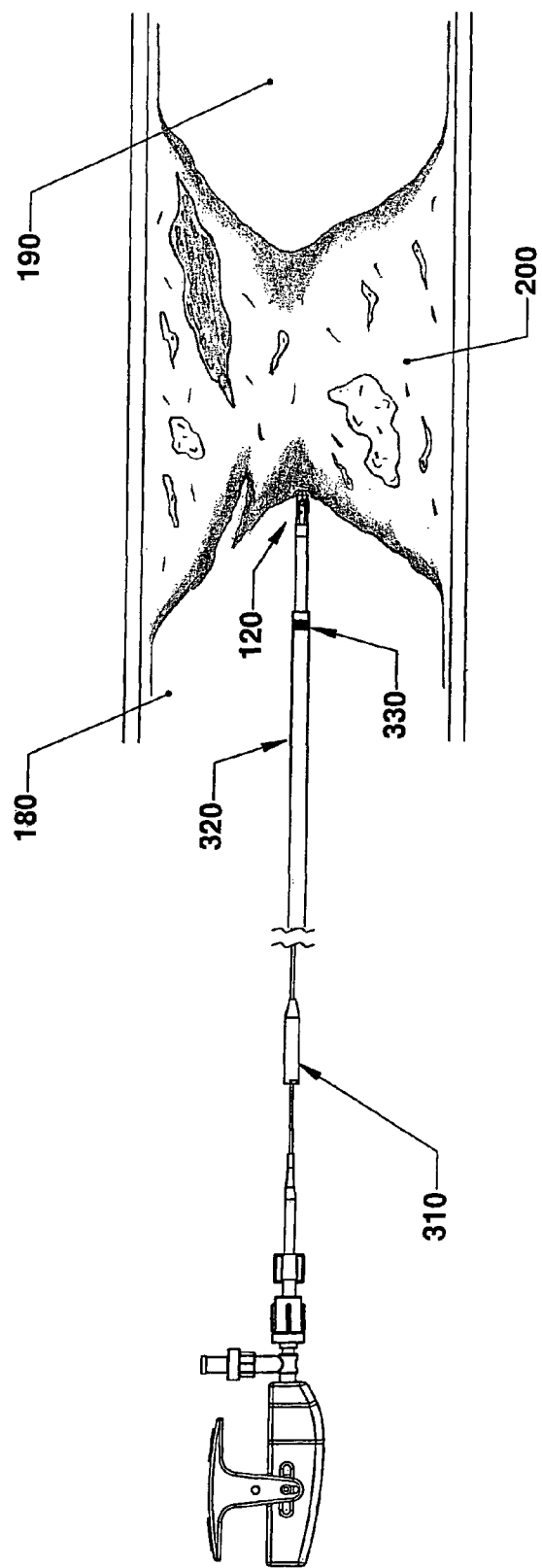
FIG. 2a is a Blunt Dissection Catheter and Sheath Catheter at a proximal end of a vascular occlusion in vasculature, under an embodiment.

FIGS. 2a through 2i generally show a clinical procedure that includes use of the catheter system, under an embodiment. FIG. 2a is a catheter system including the Blunt Dissection Catheter and Sheath Catheter at a proximal end of a vascular occlusion in vasculature, under an embodiment. The Blunt Dissection Catheter 100 and Sheath Catheter 300 are advanced concurrently to approach a vascular total occlusion 200. Proximal to the vascular occlusion 200 is the proximal true lumen of the vessel 180, and distal to the occlusion 200 is the distal true lumen of the vessel 190. The working element 120 of the Blunt Dissection Catheter 100 is advanced until it is brought into opposition to the vascular occlusion 200. To provide support to the Blunt Dissection Catheter 100, the distal end 330 of the Sheath Catheter 300 is maintained approximately a few centimeters proximal to the distal end of the Blunt Dissection Catheter 100. Axial force is applied to the Blunt Dissection Catheter 100 by the physician to establish appropriate engagement of the Blunt Dissection Catheters working element 120 into the occlusion 200.

Figure 2B:
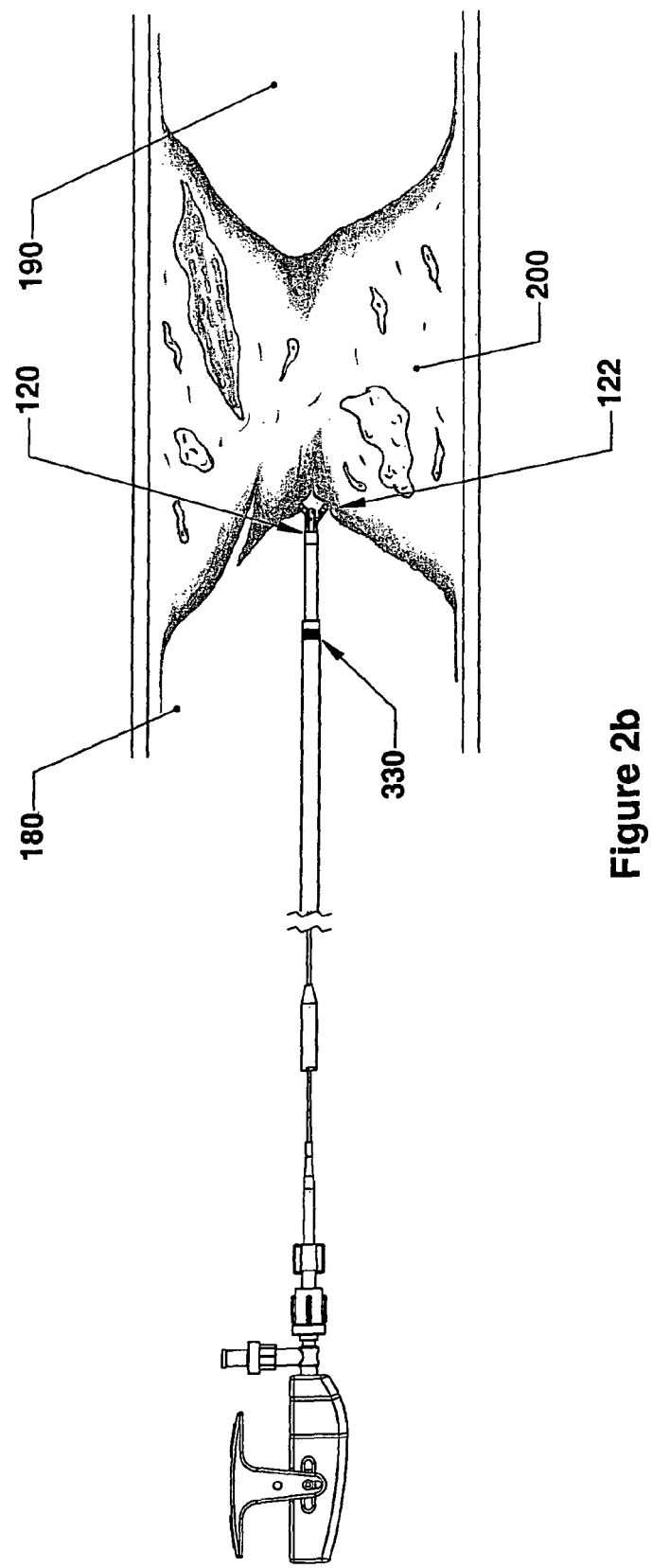
FIG. 2b is a Blunt Dissection Catheter advancing through a vascular occlusion with the Sheath Catheter maintained proximal to the vascular occlusion, under an embodiment.
Figure 2C:
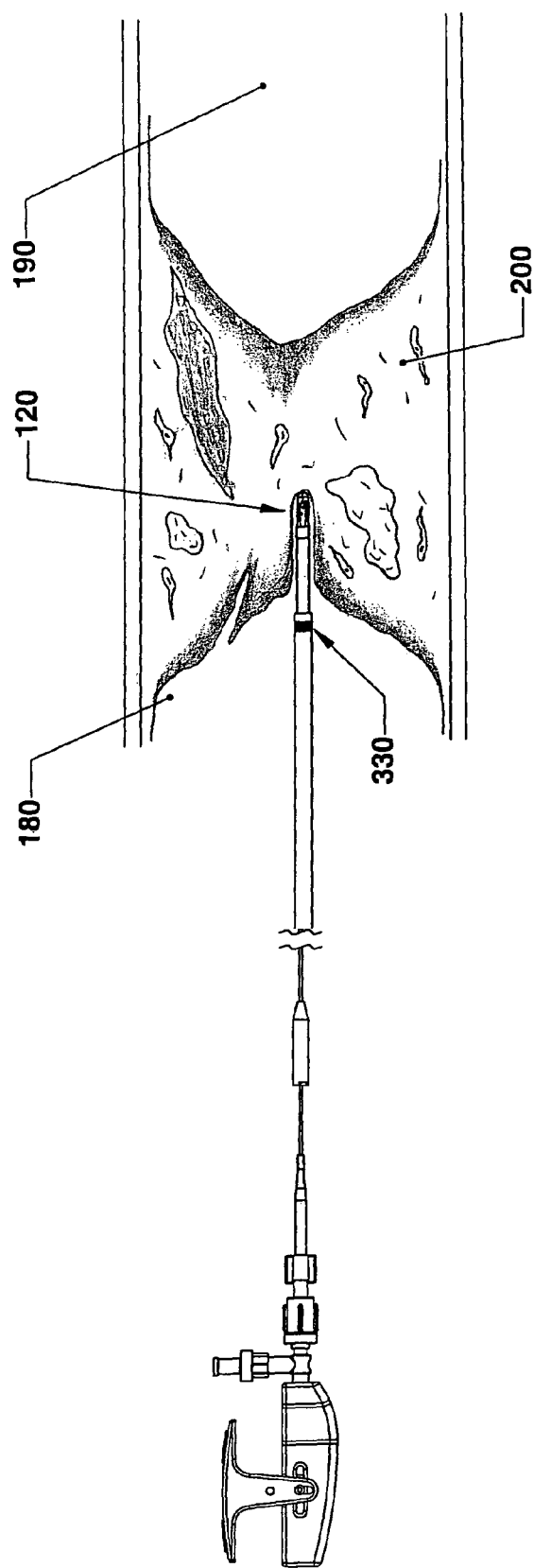
FIG. 2c is a Blunt Dissection Catheter advancing through a vascular occlusion, under an embodiment.
Figure 2D:
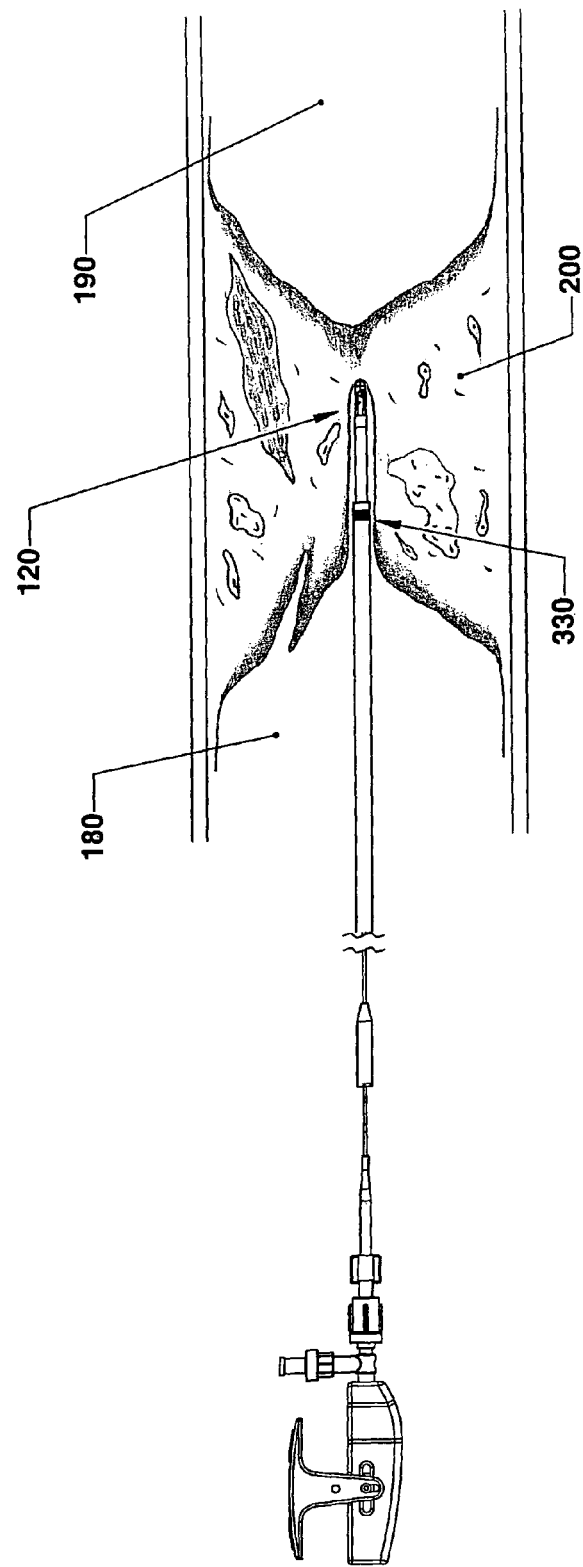
FIG. 2d is a Blunt Dissection Catheter and Sheath Catheter advancing through a vascular occlusion, under an embodiment.

FIG. 2b is a Blunt Dissection Catheter advancing through a vascular occlusion with the Sheath Catheter maintained proximal to the vascular occlusion, under an embodiment. FIG. 2c is a Blunt Dissection Catheter advancing further through a vascular occlusion, under an embodiment. FIG. 2d is a Blunt Dissection Catheter and Sheath Catheter advancing through a vascular occlusion, under an embodiment.

Upon placement of the catheter system proximate to the vascular occlusion 200, the user actuates the spreading members 122 of the Blunt Dissection Catheter 100 via the handle mechanism 110, urging the tissue in contact with the spreading members 122 to fracture, thus producing a small local dissection in the occlusion immediately distal to the working element 120 (FIG. 2b). The spreading members 122 are then closed producing an atraumatic, bullet-shaped distal tip suitable for distal advancement into the dissection track (FIG. 2c). The process of engaging the working element 120 into the occlusion with the spreading members 122 closed, followed by actuating the spreading members 122 to an open position, and subsequent closing of the spreading members 122 and advancement into the dissection track is repeated as the working element 120 of the Blunt Dissection Catheter 100 is advance through the vascular occlusion 200. The Sheath Catheter is also advanced through the vascular occlusion 200 as appropriate to the procedure (FIG. 2d).

Figure 2E:
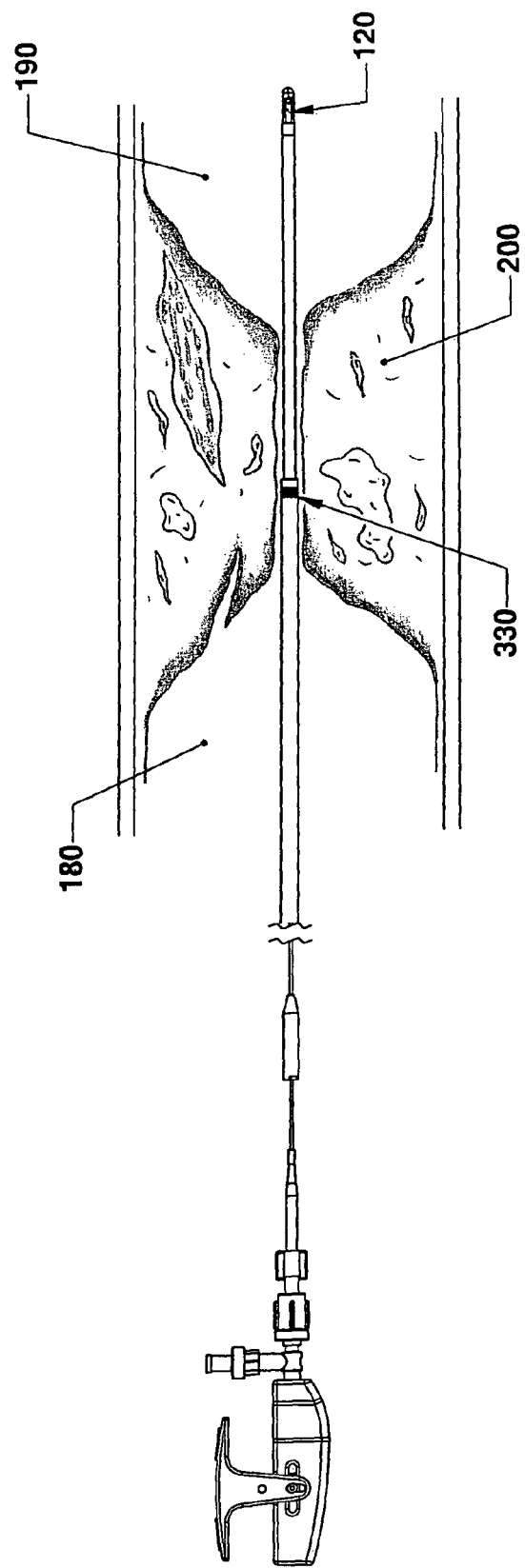
FIG. 2e is a Blunt Dissection Catheter exiting a vascular occlusion with the Sheath Catheter within the vascular occlusion, under an embodiment.

FIG. 2e is a Blunt Dissection Catheter exiting a vascular occlusion with the Sheath Catheter within the vascular occlusion, under an embodiment. As a dissection track is produced in/through the occlusion 200, and the Blunt Dissection Catheter 100 is advanced distally, the Sheath Catheter 300 can also be advanced into the dissection track within the occlusion 200.

Figure 2F:
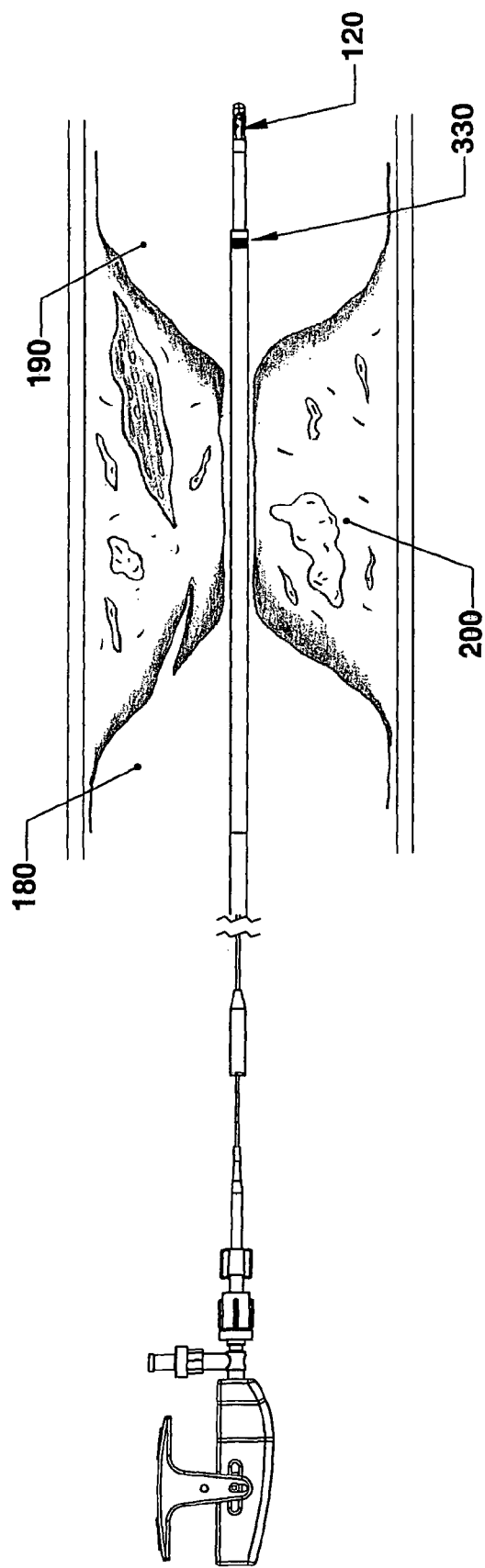
FIG. 2f is a Blunt Dissection Catheter and Sheath Catheter both advanced through a vascular occlusion, under an embodiment.
Figure 2G:
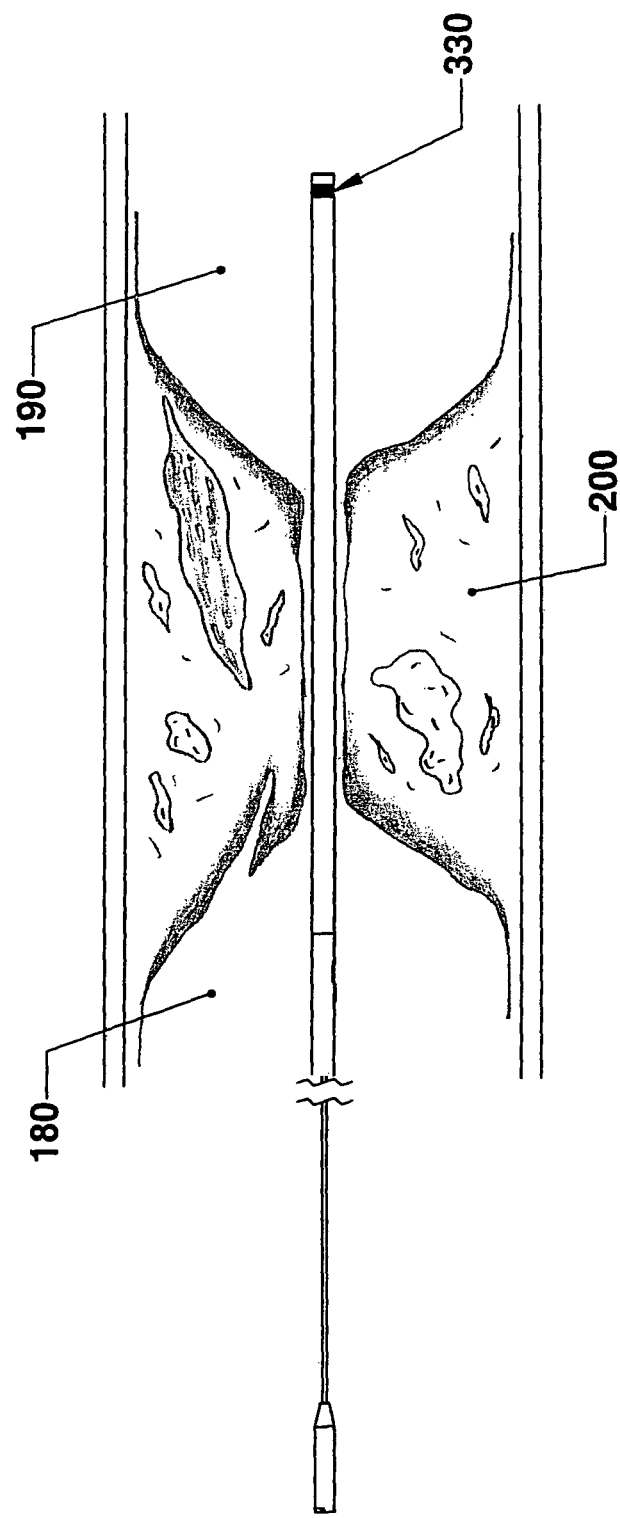
FIG. 2g is a Sheath Catheter maintaining position across vascular occlusion following removal of a Blunt Dissection Catheter, under an embodiment.

FIG. 2f is a Blunt Dissection Catheter and Sheath Catheter both advanced through a vascular occlusion, under an embodiment. The distal tip 330 of the Sheath Catheter 300 has been advanced over the Blunt Dissection Catheter 100 and beyond the total occlusion 200. At this point, the Blunt Dissection Catheter 100 may be fully retracted and removed from the vasculature, leaving the Sheath Catheter 300 in place across the vascular occlusion, with the distal tip 330 distal to the occlusion 200. FIG. 2g is a Sheath Catheter maintaining position across the vascular occlusion following removal of the Blunt Dissection Catheter, under an embodiment.

Figure 2H:
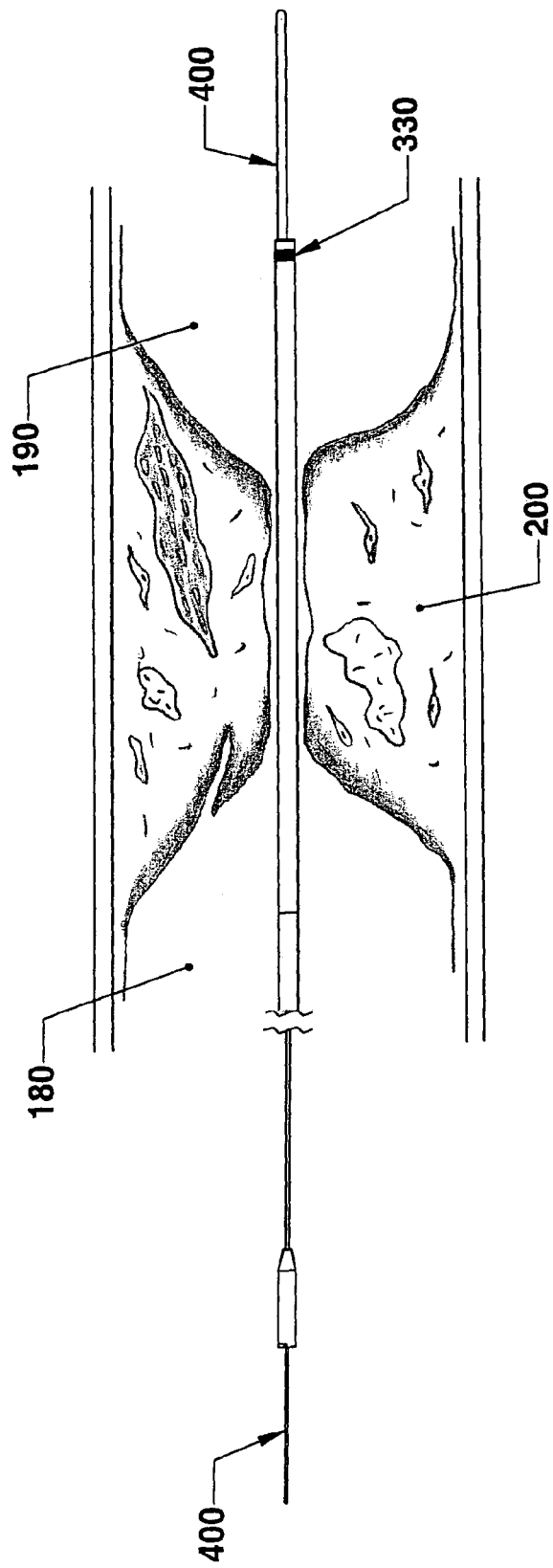
FIG. 2h is a guide wire advanced through the Sheath Catheter and into a vessel true lumen distal to an occlusion, under an embodiment.
Figure 2I:
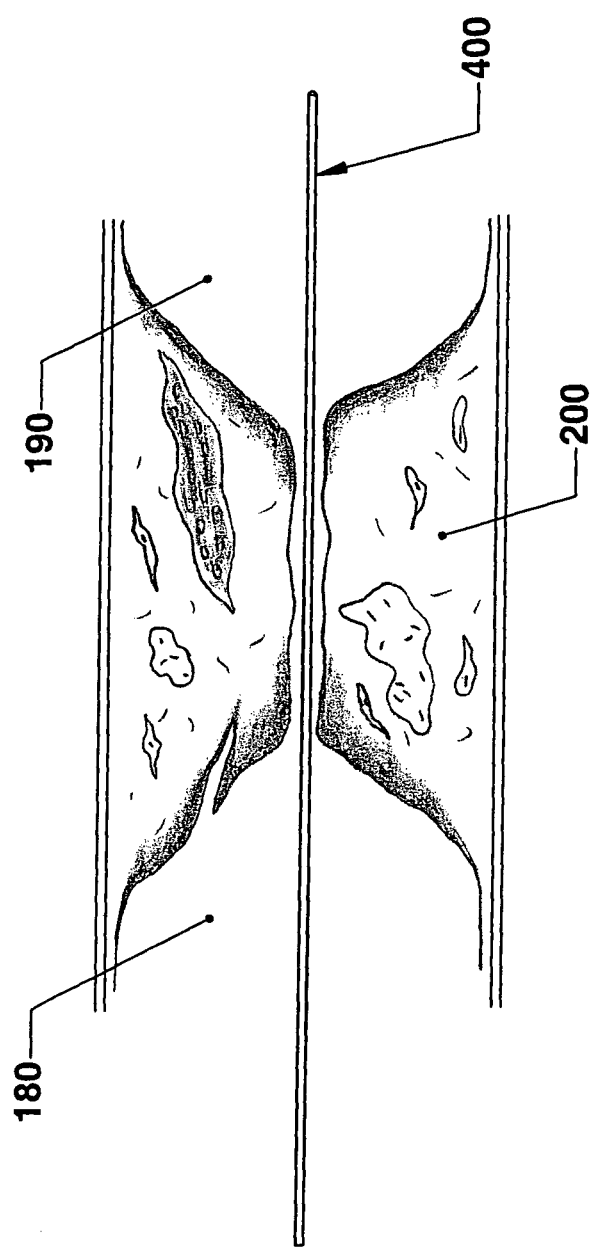
FIG. 2i is a guide wire in place across a vascular occlusion following removal of a Sheath Catheter, under an embodiment.

FIG. 2h is a guide wire advanced through the Sheath Catheter and into a vessel true lumen distal to an occlusion, under an embodiment. The guide wire 400, which can be any of a number of guide wire types known in the art, is advanced through the lumen of the Sheath Catheter 300 and into the true lumen 190 of the vessel distal to the occlusion 200. Following placement of the guide wire, the Sheath Catheter 300 is removed from the vasculature, leaving the guide wire 400 in place across the occlusion 200. The guide wire is now positioned to deliver therapeutic treatment modalities to the vascular site, such as angioplasty balloons, athrectomy devices, or stents. FIG. 2i is a guide wire in place across a vascular occlusion following removal of a Sheath Catheter, under an embodiment.

In the prior discussion, the Blunt Dissection Catheter and Sheath Catheter are delivered to the site of the vascular occlusion together, i.e. the Blunt Dissection Catheter is loaded within the Sheath Catheter for/during delivery. This configuration applies when using the system in either coronary or peripheral vessels. However, for applications in which the vasculature has a high degree of tortuosity, as is more often seen in certain coronary anatomies, an alternate method of gaining access to the site of the vascular occlusion may be desirable. If the tortuosity of the vasculature is too extreme for the Blunt Dissection Catheter and the Sheath Catheter to navigate as a system, it may be desirable to deliver the Sheath Catheter first via a more flexible delivery scheme, and to subsequently deliver the Blunt Dissection Catheter within the Sheath Catheter to the site of the vascular occlusion. The Sheath Introducer includes very flexible polymers and thus the Sheath Catheter/Sheath Introducer combination can afford a greater degree of flexibility at the distal end of the assembly to allow tracking through higher degrees of vascular tortuosity while delivering the distal end of the Sheath Catheter to the desired vascular location.

In this alternate approach, the Sheath Catheter is delivered first directly to the site of the vascular occlusion via a conventional guide wire. However, whereas the diameter of a typical coronary guide wire is 0.014 inches, and the nominal inner diameter of the Sheath Catheter is approximately 0.041 inches, the Sheath Catheter may not be tracked directly and safely over the guide wire since the Sheath Catheters leading distal edge would be greatly exposed. This exposed leading edge may lead to skiving of the vessel wall as it is advanced in the vasculature. To protect the vessel wall from damage by the leading edge of the Sheath Catheter, the Sheath Catheter is internally supported by a Sheath Introducer (also referred to as an obturator).

The Sheath Introducer is a single lumen sleeve that fits snugly within the Sheath Catheter along a portion of the length of the Sheath Catheter, and incorporates a guide wire lumen to accommodate standard vascular guide wires. The distal segment of the Sheath Introducer may extend from approximately 0.5 cm to 3 cm beyond the distal end of the Sheath Catheter, but is not so limited. The distal segment of the Sheath Introducer includes at least one a tapered distal end to facilitate its tracking and a rounded distal end to be more atraumatic.

In a first embodiment, the Sheath Introducer is designed with a uniform outer diameter that runs the entire length up to the proximal hub. This allows for easy removal of the Sheath Introducer from the Sheath Catheter once delivered to the site of the vascular occlusion.

In an alternative embodiment, the diameter of the Sheath Introducer sleeve that resides within the Sheath Catheter is a first uniform diameter, and only the distal segment of the Sheath Introducer extending from the distal end of the Sheath Catheter may be of a second, slightly increased diameter, such that the transition from Sheath Introducer to Sheath Catheter forms a smooth constant diameter. In this configuration, the distal segment of the Sheath Introducer may still be terminated as described above.

The proximal end of the Sheath Introducer of an embodiment terminates with a simple hub including a standard luer connector with a central lumen that communicates with the guide wire lumen of the single lumen sleeve. The proximal hub of the Sheath Introducer can also be press fit into the Sheath Catheters proximal hub to maintain the Sheath Catheter and Sheath Introducer in proper axial registration, i.e. to maintain the 1 cm to 5 cm of Sheath Introducer extension beyond the distal end of the Sheath Catheter during use.

In preparation for introducing the Sheath Catheter into the vasculature, the distal end of the Sheath Introducer is loaded into the proximal hub of the Sheath Catheter and advanced until the Sheath Introducer hub is press fit into the Sheath Catheter hub. In this configuration the Sheath Introducers distal segment extends approximately 1 cm to 5 cm beyond the Sheath Catheters distal tip to facilitate tracking of the combined assembly over a guide wire, but is not so limited. Once at the desired vascular location, the Sheath Introducer and guide wire may be fully retracted, leaving the Sheath Catheter in place at the desired vascular site. Concerning the embodiment wherein the Sheath Introducer distal segment is equal in diameter to the Sheath Catheter outer diameter, the Sheath Introducer tip may be fabricated of a sufficiently low durometer polymer such that upon retraction, the tip may be slightly compressed as the Sheath Introducer is removed from the Sheath Catheter.

Durometer as used herein is a measure of material hardness, but other definitions known in the art are included as appropriate. Consequently, the durometer of a polymer is a measure of the hardness of the polymer. Therefore, durometer relates to a measure of the stiffness of a device formed with the polymer. As an example, catheter shafts laminated with higher durometer polymers afford a comparatively higher stiffness than catheter shafts laminated with lower durometer polymers. Further, catheter shafts laminated with the lower durometer polymers afford a comparatively higher degree of flexibility than catheter shafts laminated with higher durometer polymers.

The Sheath Introducer sleeve of an embodiment is formed from a single extrusion of one or more polymers including at least one of Teflon (PTFE), High Density Polyethylene (HDPE), Low Density Polyethylene (LDPE), and any of a number of combinations of these materials, but the Sheath Introducer is not limited to these polymers. One or more of the polymers of an embodiment are lubricious. These polymers may also be graded to provide lesser durometer polymers at the distal end of the Sheath Introducer to afford a higher degree of flexibility. Fabricating a very flexible distal end of the Sheath Introducer is a desirable feature since it will more easily track over the guide wire, and allow the Sheath Introducer/Sheath Catheter system to track more easily in general. Alternatively, the Sheath Introducer may be fabricated of a braided material (stainless steel, polymer filaments) laminated with similar polymers.

When tracking the Sheath Introducer/Sheath Catheter to a target vascular site, the distal end of the Sheath Introducer is the leading end of the system. Therefore the Sheath Introducer/Sheath Catheter of an embodiment includes a fluoroscopic marker in/on a distal segment of the Sheath Introducer. Fluoroscopic marking components such as thin-walled Platinum bands having a thickness of approximately 0.001 to 0.002 inches and a length of approximately 0.5 millimeters (mm) to 2 mm can be embedded within the distal polymer of the Sheath Introducer, or alternatively affixed to the Sheath Introducer with medical adhesives. The bands can also be fabricated from stainless steel and coated with gold. Alternatively, the bands can be embedded into the inside surface or outside surface of the sleeve polymer using swaging methods. Alternatively, fluoroscopic inks can be printed on the distal surface of the Sheath Introducer to provide a similar fluoroscopic marking indicator. This fluoroscopic image provides the physician with information to indicate when the Sheath Introducer/Sheath Catheter has reached the proximal end of the vascular occlusion.

The Sheath Catheter of an embodiment includes a shaft system and a proximal luer hub, but is not so limited. The shaft system comprises components including an inner polymer layer, a middle layer, an outer polymer layer, a distal fluoroscopic marking system, and an external lubricious coating, but is not so limited. Each of these components is described below.

Regarding the shaft system of an embodiment, the inner polymer layer forms the interior surface of the Sheath Catheter. To facilitate the advancement and retraction of the Blunt Dissection Catheter, or other catheters within the Sheath Catheter, this inner layer includes a lubricious material, such as Telfon (PTFE), polyimides, and Polyethylenes including High Density Polyethylene (HDPE), Low Density Polyethylene (LDPE), and/or a blend of the two, but is not limited to these materials. These polymers are commonly used in the medical device field. The inner polymer layer can be chosen to be of the same material and durometer throughout the length of the Sheath Catheter, or polymers may be chosen to customize the desired operational attributes (flexibility, torque control) of particular regions along the Sheath Catheter.

The middle layer of the shaft system of an embodiment includes braided filaments, such as stainless steel wire, Nitinol wire, Kevlar or Dacron fiber, but is not so limited. The braided filaments form a mesh tube that serves as a supporting structural component to provide hoop strength to the shaft system. The filaments used to produce this mesh tube include at least one of flat, square, and round configurations, as well as combinations of these filaments. The number of individual filaments may practically vary from approximately eight (8) to 32 (thirty-two) filaments, but are not necessarily so limited.

Any filament material can be used that provides the required hoop strength to maintain the tubular configuration of the catheter shaft. The number of filaments per inch (pics) may be adjusted to be consistent along the entire length of the catheter shaft, or the pics may be varied to set the desired operational attributes (flexibility, torque control) of the catheter. Generally, lower pic counts are associated with less torque control, greater flexibility and less hoop strength. Alternatively, higher pic counts are associated with greater torque control, less flexibility and greater hoop strength. In an embodiment the number of pics may range from approximately 80 to 120 pics per inch.

The outer polymer layer of the shaft system forms the exterior surface of the Sheath Catheter. This polymer is selected from a variety of commonly used polymers in the medical device field including at least one of nylons, polyurethanes, polyethylenes, polyimides, Pebax, Grilamids or carbothanes, but the outer polymer layer is not so limited. Material of the outer polymer layer is selected to set the desired operational attributes (flexibility, torque control) of the catheter. The polymer of the outer layer may be chosen to be of the same material and durometer throughout the length of the Sheath Catheter, or the outer layer of polymer can be chosen to provide varying operational characteristics for different regions or sections of the catheter shaft.

Specifically, relative to proximal sections of the catheter shaft, the distal section of the catheter shaft may generally require a greater degree of flexibility to facilitate tracking through vascular tortuosity (especially coronary). Alternatively, the proximal section of the catheter shaft can require greater push and torque control characteristics to facilitate advancing the catheter further distally in the vasculature. To accomplish these operational attributes, polymers of varying durometers are selected for the proximal and distal sections of the catheter. For example, lower durometer polymers form one or more distal sections of the catheter shaft to facilitate flexibility, and higher durometer polymers form one or more proximal sections of the catheter shaft to facilitate push and torque control. Another material which serves more specifically to support push and torque control at the proximal section of the catheter is polyimide, which cannot typically be re-formed using heat, as can the aforementioned thermoform polymers.

During fabrication of the main shaft of a Sheath Catheter that includes an inner polymer, a tubular braid and an outer polymer laminate as described above, the outer surface of the inner polymer liner and inner surface of the outer polymer laminate are physically connected or bonded to each other. This connection takes place between the cross-over points of the braid wire that forms the braided tubular member. The physical bonding of these two surfaces through the braided tubular member produces a unified construction of the Sheath Catheter shaft. However, a challenge exists in that the materials used for the inner liner of an embodiment, namely polytetrafluoroethylene (PTFE), high density polyethylene (HDPE) or low density polyethylene (LDPE) are all very resistant to bonding to other polymers.

In a first embodiment, this challenge is overcome when using PTFE as the inner liner by etching the outer surface of the PTFE tube with an acid to produce microscopic interstices on the surface into which the outer polymer laminate may bond. If Pebax or nylons are used for the outer laminate, the processing temperature may range from approximately 400 degrees Fahrenheit (F) to 450 degrees F., which is sufficient to flow these polymers, but will not be so hot as to flow the PTFE liner, nor the interstices present on the outer surface of the inner. During lamination of the outer polymer onto the Sheath Catheters shaft, the outer polymer laminate flows through or between the cross-over points of the braid wire and onto the outer surface of the inner PTFE liner. The thickness of the outer polymer laminate is adjusted so that the braid wire is then completely contained within the outer laminate, and the outer polymer laminate forms a smooth uninterrupted surface. During the cooling process of lamination, the inner surface of the outer polymer becomes "locked" into the interstices of the inner polymer liner, thus connecting the two polymers between the braid wire.

In an alternative embodiment in which the inner polymer liner is composed of high density or low density polyethylene, the Sheath Catheter shaft can be laminated with either of the same materials. Since these materials have common melting temperatures, the inner polymer liner and outer polymer laminate will bond easily to each other, producing a unified shaft construction.

The shaft system of an embodiment includes a distal fluoroscopic marking system to indicate the distal end of the catheter when being viewed under fluoroscopy. One type of marking system includes a platinum ring (wall thickness typically approximately 0.001 to 0.002 inches; length typically approximately 0.5 mm to 2 mm) embedded within the polymers at the distal end of the catheter. Alternatively, the ring is fabricated from stainless steel and coated with gold. The ring is placed on either the inside or outside of the braided tubular mesh, and laminated with either the inner layer polymer or the outer layer polymer.

An alternative marking system uses a platinum coil. The platinum coil is placed in a similar manner to the platinum band described above, but is not so limited.

Another alternative marking system uses radiopaque adhesives or compounds printed onto the surface of either the inner polymer, the braided tubular mesh, or the outer polymer. These adhesives typically employ the use of tantalum, bismuth, gold, silver or platinum, but are not so limited.

Yet another alternative marking system includes a gold coating. The gold coating is positioned over the distal section of the tubular mesh, but may be positioned differently in alternative embodiments.

Still another alternative marking system includes use of fluoroscopic material in materials of the shaft system (bismuth for example). In one embodiment, the fluoroscopic material is impregnated into the structural polymers which laminate the distal end of the Sheath Catheter.

Regarding the external lubricious coating of the shaft system described above, the surface of the outer polymer may be coated with a lubricious material such as a silicone dispersion or, alternatively, a hydrophilic coating (Surmodics). Whereas the interior surface of diseased vessels may contain fibrotic material, calcium, and/or the inner diameter of the vessel may be greatly reduced, the coating acts to further facilitate delivery of the catheter through the vasculature by reducing friction between the catheters external surface and the interior surface of the vessel.

The proximal female hub of the Sheath Catheter system includes a standardized luer connector. The luer connector supports connection to other standardized interventional devices; for example, a syringe couples to this hub to flush the catheter prior to use. The proximal hub is fabricated of a number of polymers commonly used in medical devices, an example of which is polycarbonate.

The Sheath Catheter of an embodiment has an outer diameter in a range of approximately 0.050 to 0.070 inches, but is not so limited. A nominal outside diameter is approximately 0.0560 inches.

The Sheath Catheter of an embodiment has an inner diameter in a range of approximately 0.035 to 0.050 inches, but is not so limited. A nominal inner diameter is approximately 0.040 inches.

The Sheath Catheter of an embodiment has a working length in a range of approximately 80 cm to 150 cm, but is not so limited. A nominal working length is approximately 130 cm.

The catheter fabrication process of an embodiment includes polymers of the inner and/or outer layers that flow within the spaces in the braided tubular mesh (middle layer). In this manner the inner polymer fuses with the outer polymer, forming bridges across the mesh tube. This produces an integral shaft lamination that provides increased strength, torque control and reliability to the shaft construction.

As described above, the polymers forming the catheter shaft of an embodiment include polymers of varying durometers that allow for tailoring of specific operational attributes of different sections of the catheter shaft. Further, the grading of the polymers from the proximal to the distal end of the catheter may incrementally decrease. As an example, a proximal region of the catheter shaft (the proximal most approximately 80 cm) is laminated with Grilamid, followed by a region (length approximately 8 cm) of 73D Pebax, followed by a region (length approximately 8 cm) of 63D Pebax, followed by a region (length approximately 5 cm) of 55D Pebax. In this manner, the transition from one polymer to the next is gradual, and the flexibility of the catheter shaft gradually increases.

Figure 3A:
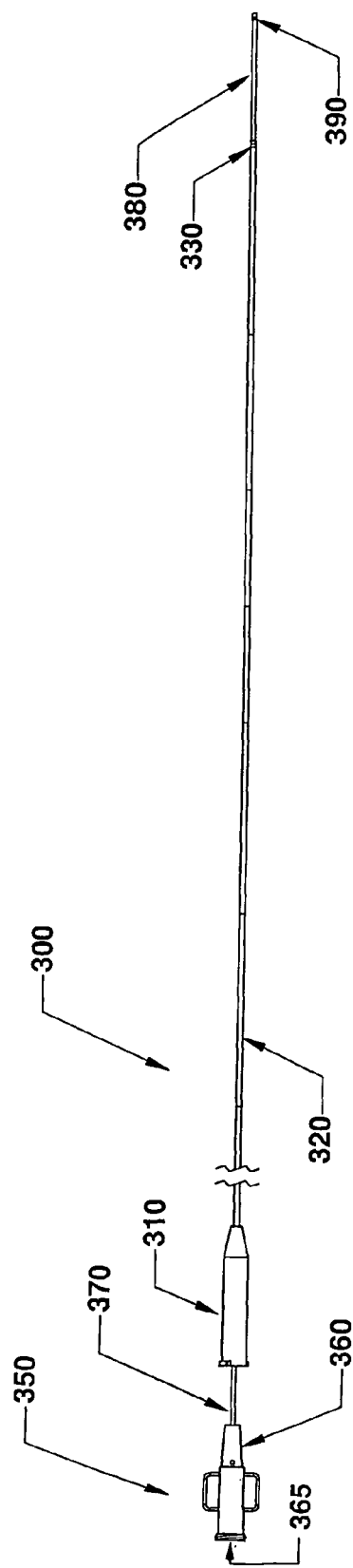
FIG. 3a is a catheter system including a Sheath Catheter and a Sheath Introducer, under an embodiment.

FIG. 3a is a catheter system including a Sheath Catheter 300 and a Sheath Introducer 350, under an embodiment. The Sheath Catheter 300 and Sheath Introducer 350 are shown as a system, but are not so limited. In this configuration, the system is trackable over a conventional guide wire, via a central lumen 365 of the Sheath Introducer 350, to deliver the Sheath Catheter distal end 330 proximate to the site of a vascular occlusion. The Sheath Introducer 350 is shown with the hub 360 retracted proximally for visual clarity of the components. During use however, the Sheath Introducer hub 360 can be press fit into the Sheath Catheters hub 310, locking the Sheath Catheter 300 and Sheath Introducer 350 together. In this configuration, a distal segment 380 of the Sheath Introducer 300 extends from the Sheath Catheter distal end 330 by approximately 0.5 cm to 5 cm, but is not so limited. Following tracking over a conventional guide wire to the target vascular site, the guide wire and Sheath Introducer 350 are removed, leaving the distal end of the Sheath Catheter 330 in place proximal to the vascular occlusion where it is positioned to serve as the conduit through which another catheter like the Blunt Dissection Catheter 100 can be delivered to the vascular occlusion.

Although the Sheath Catheter 300 is described as working in conjunction with a Blunt Dissection Catheter 100, once in place at the vascular site the Sheath Catheter 300 can be used to deliver other types of catheter systems or apparatus known in the art which are dimensionally compatible with the Sheath Catheter 300. As an example, conventional guide wires may be delivered first, if desired, in an attempt to first cross the occlusion prior to usage of the Blunt Dissection Catheter 100. If the guide wire is unsuccessful in crossing the occlusion, the guide wire may be removed, and the Blunt Dissection Catheter 100 may be advanced within the Sheath Catheter 300 for use in crossing the occlusion.

Figure 3B:
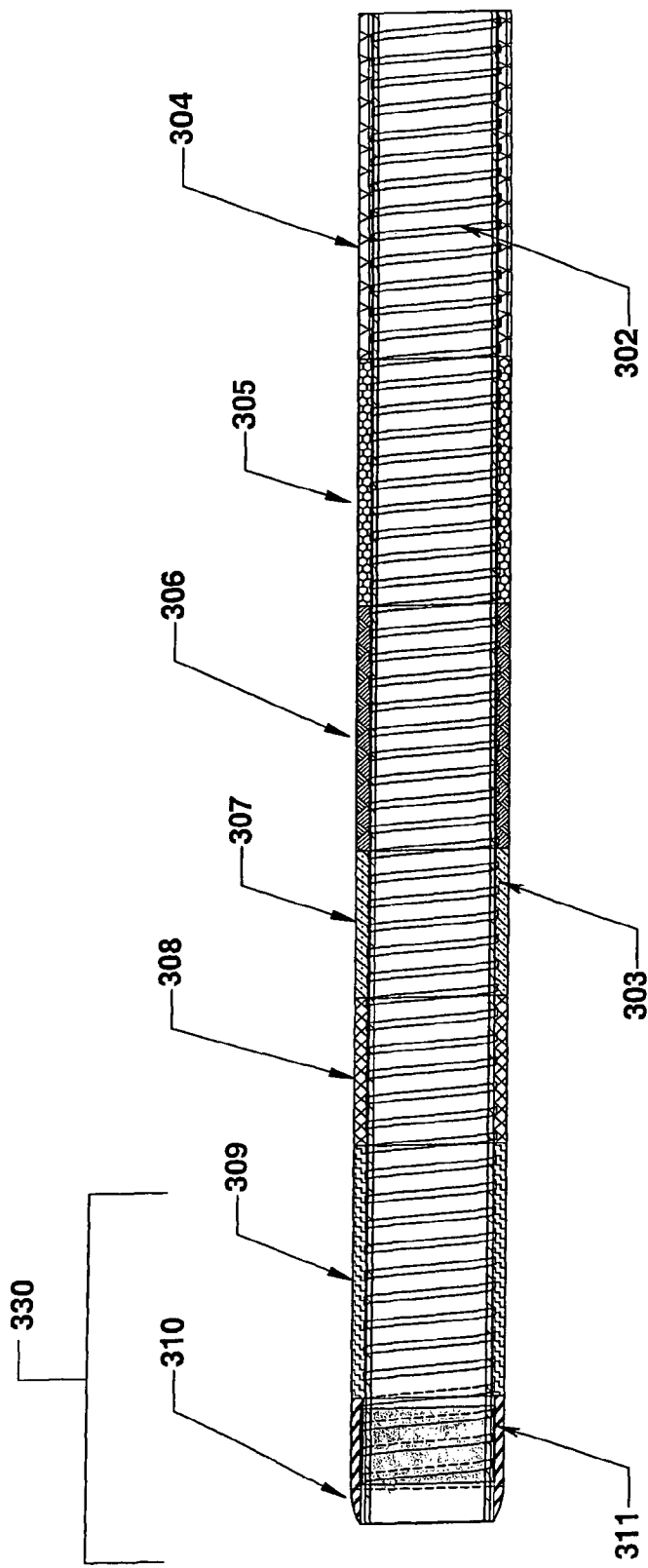
FIG. 3b is a longitudinal cross-section of a distal segment of a Sheath Catheter, under an embodiment.

FIG. 3b is a longitudinal cross-section of a distal segment of a Sheath Catheter 300, under an embodiment. The shaft of the Sheath Catheter 300 includes an inner polymer liner 303 over which wire 302 is braided. The shaft is then laminated with another polymer (304-309). As an operational objective of the Sheath Catheter 300 is to provide a very flexible distal segment, the outer polymer laminate may be graded from relatively higher durometer polymers in the proximal section to relatively lower durometer polymers in the distal section. As an example, the shaft includes six separate outer laminates in sections 304 through 309. The outer laminate of section 304 is fabricated using Pebax 63D, followed by the outer laminate of section 308 that is fabricated of a lower durometer polymer, possibly Pebax 55D, followed by the outer laminate of section 307 that is Pebax 40D, and so on, gradually decreasing the durometer of the outer laminate polymer until the distal segment 330 of the Catheter Sheath 300 is reached. While six graded polymers are described in this embodiment, a lesser or greater number of polymers can be used to provide the correct physical attributes for the shaft.

Another material for use in the catheter shafts of alternative embodiments includes polyethylene, where the polyethylene is graded as appropriate to the intended use of the catheter system. In another embodiment, polymer types can be alternated to achieve the appropriate flexibility.

The inner polymer layer 303 of an embodiment includes a highly lubricious material since the inner lumen of the Sheath Catheter 300 is used to shuttle other devices. The inner liner 303 can be fabricated of polytetrafluoroethylene (PTFE) or high density polyethylene (HDPE) as examples, but is not so limited. The durometer of the inner liner 303 may also be graded as described above to provide the appropriate degree of flexibility. As an example, low density polyethylene (LDPE) might be used in the most distal segment 330 of the Sheath Catheter 300 to provide a higher degree of flexibility than HDPE.

The choice of braiding materials depends upon the torque control, flexibility, hoop strength and wall thickness appropriate to a specific application. For example, the braid wire can be 0.001 inch by 0.003 inch flat stainless steel wire as an example. The braid wire can also be 0.002 inch round wire. Round braid wire affords a higher degree of overall flexibility, hoop strength and torque control to the Sheath Catheter shaft construction. However, the round wire generally results in a catheter shaft having a greater overall wall thickness as compared to the flat wire version. Alternative braid materials can also be used such as Dacron fibers, or other suitable polymers; these alternative materials generally do not afford the same degree of toque control or hoop strength but can increase the overall flexibility of the Sheath Catheter shaft.

The lay-up of the distal segment 330 of the Sheath Catheter 300, including the atraumatic tip 310 and fluoroscopic marker band 311 is as follows. The fluoroscopic marker band 311 is affixed to the Sheath Catheter shaft in numerous ways. In one embodiment the marker band 311 is external to the wire braiding 302, but is laminated over with the outer polymer layer 309. The marker band 311 is thus encapsulated within the outer polymer lamination, which provides a smooth surface to the distal segment 330 of the Sheath Catheter. Continuing with this embodiment, the distal end of the wire braiding 302 and the distal end of the marker band 311 can also terminate concurrent with each other. Additionally, the inner polymer liner 303 may extend from approximately 1 mm to 10 mm beyond the end of the marker band 311 and braid wire 302, but is not so limited. To complete the fabrication, the outer polymer 309 is continued distally over the marker band 311 to form an atraumatic polymer tip 310 that terminates concurrent with the distal end of the inner liner 303. Thus, the length of the atraumatic tip 310 is equal to the length the inner polymer liner 303 and outer polymer laminate 309 extended beyond the marker band 311.

The shape of the atraumatic tip 310 is completed by rounded or tapering the distal annular edge of the outer polymer laminate. This process is commonly referred to as tip-forming and may be performed by placing the fabricated assembly in a heated glass mold, the internal contour of which has been-fashioned with the final desired tip shape. When placed in the mold, the outer laminate is heated to allow the outer laminate to just begin to soften and take the interior shape of the mold. The catheter tip 310 remains in the mold while the mold cools, setting the atraumatic tapered or rounded shape into the distal tip 310 of the Sheath Catheter 300. Upon completion of the cooling, the catheter tip 310 is removed from the mold. Methods to locally heat the mold may be via conventional convection heating, or alternatively, radio frequency energy may be used to locally heat the atraumatic tip 310.

The dimensions of the makerband(s) may generally range from approximately 0.05 mm to 3 mm in length, and from 0.001 to 0.003 inches in thickness, but are not so limited. Markerband(s) may be fabricated from a variety of materials. One material that provides suitable fluoroscopic imaging is platinum, or an alloy such as platinum-iridium, or platinum-tungsten. Alternatively, the markerband(s) are fabricated of stainless steel and gold coated. At the dimensions stated, stainless steel itself does not provide suitable fluoroscopic imaging, and thus it is coated with a more fluoroscopic material such as gold to provide a suitable fluoroscopic image. A layer of gold coating of approximately 0.0005 to 0.002 inches generally provides an adequate fluoroscopic image.

Figure 3C:
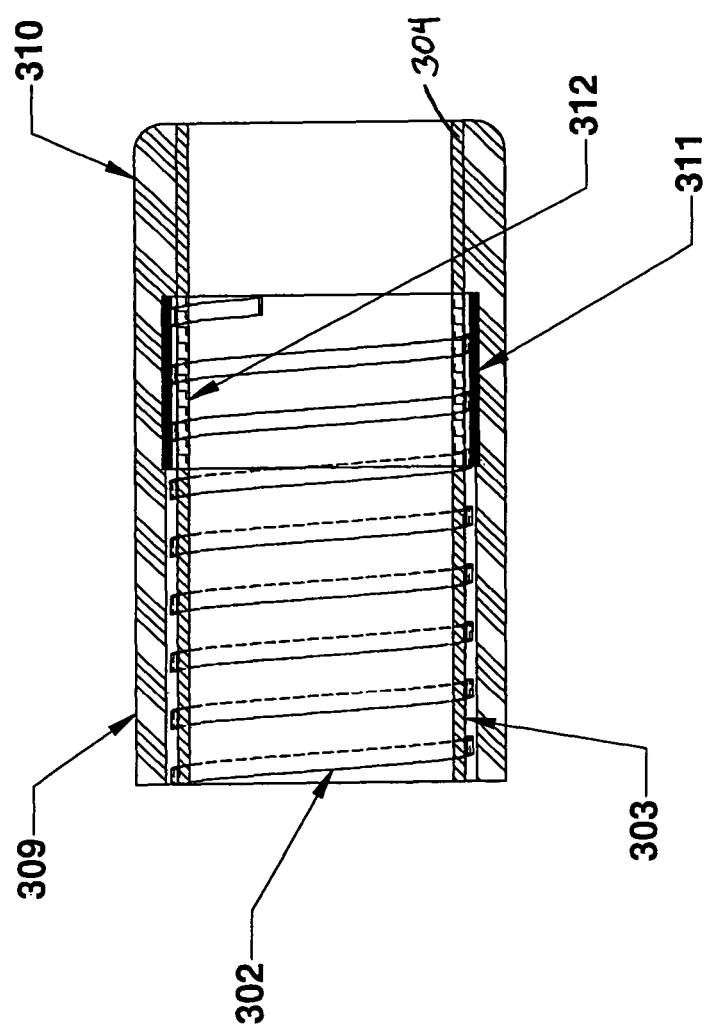
FIG. 3c is a longitudinal cross-section of a distal end of a Sheath catheter, under an alternative embodiment.

FIG. 3c is a longitudinal cross-section of a distal end of a Sheath Catheter 300, under an alternative embodiment. This embodiment includes two makerbands, an inner marker band 312 and an outer marker band 311. The inner marker band 312 is underneath the braid wire 302 and butts against a proximal section of inner polymer liner 303 and a distal section of polymer liner 304. A second markerband 311 is external to the braid wire 302. In this fashion, the braid wire 302 is sandwiched between the two markerbands, and this area may further be soldered, glued or welded to provide a secure connection of the marker bands 311/312 to the braid wire 302. As described above, the braid wire and marker bands may have a common distal termination point. Likewise, the proximal ends of the marker bands 311/312 may also have a common proximal termination point. Alternatively, the distal and/or proximal ends of either marker band may be proximal to, or distal to, the corresponding distal and/or proximal end of the other marker band. Further describing this alternative embodiment, the inner polymer liner 304 and outer polymer liner 310 can also be extended beyond the distal end of either marker band to provide an atraumatic tip as described above.

Figure 3D:
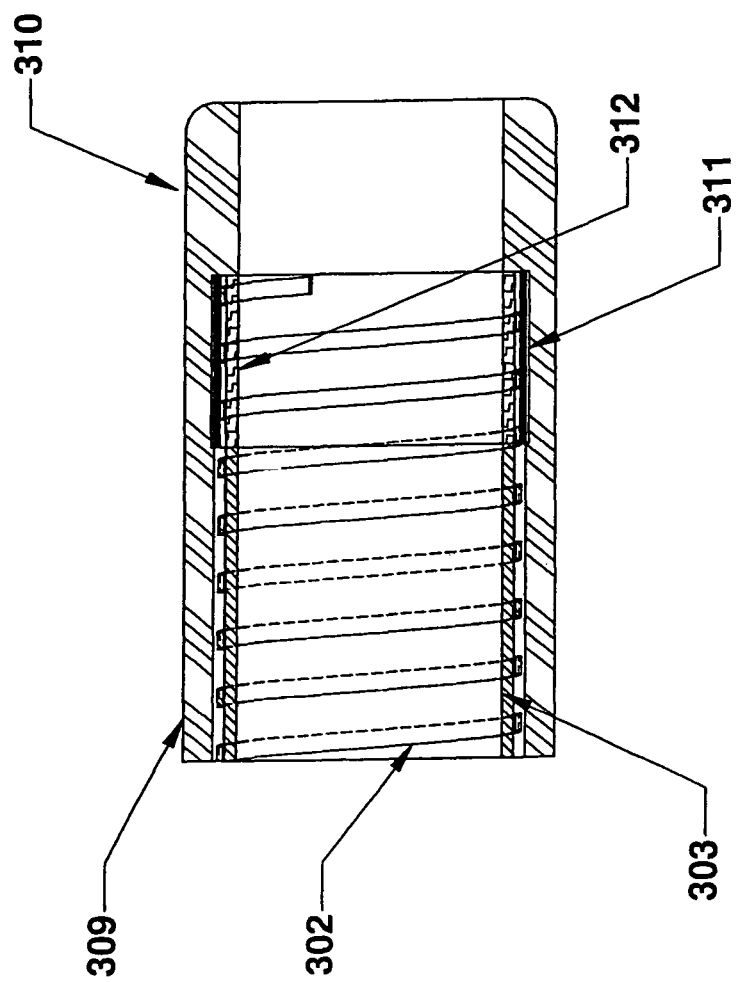
FIG. 3d is a longitudinal cross-section of a distal end of a Sheath catheter, under another alternative embodiment.

FIG. 3d is a longitudinal cross-section of a distal end of a Sheath Catheter 300, under another alternative embodiment. The inner polymer liner 303 is terminated concurrent with the distal end of either maker band(s), and the outer polymer laminate 309 extends distally beyond the marker band(s) to form the atraumatic tip 310. This embodiment may also be fabricated with the use of only one marker band 311, residing on the outside of the braid wire 302, as described above.

Figure 3E:
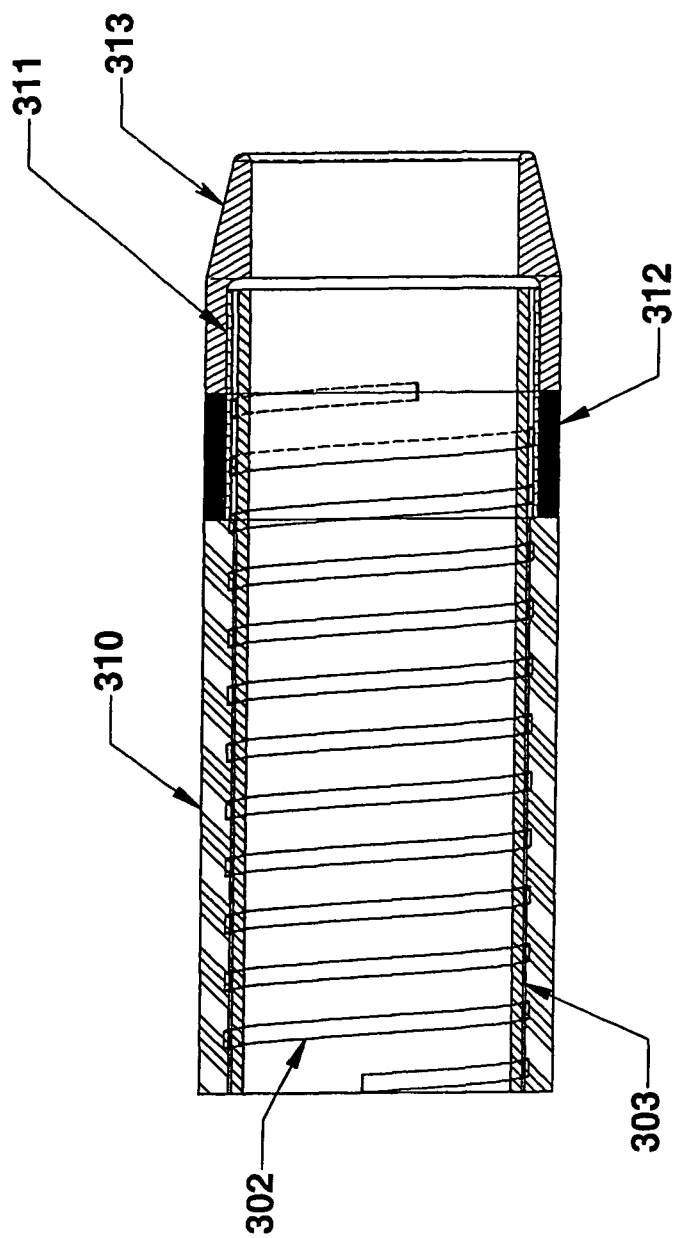
FIG. 3e is a longitudinal cross-section of a distal end of a Sheath catheter, under yet another alternative embodiment.

FIG. 3e is a longitudinal cross-section of a distal end of a Sheath Catheter 300, under yet another alternative embodiment. The distal end includes an inner marker band 312 and outer marker band 311 as described above. However, the inner markerband 312 is extended distally beyond the distal end of the outer marker band 311. This extension provides a circumferential landing for the attachment of a pre-formed metallic or polymer nosecone. A metallic nosecone may be welded or glued to the inner marker band 312, or alternatively, a polymer nosecone may be glued to the inner marker band 312 extension as well. The inner liner 303 may extend distally to terminate concurrently with the nosecone.

Figure 3F:
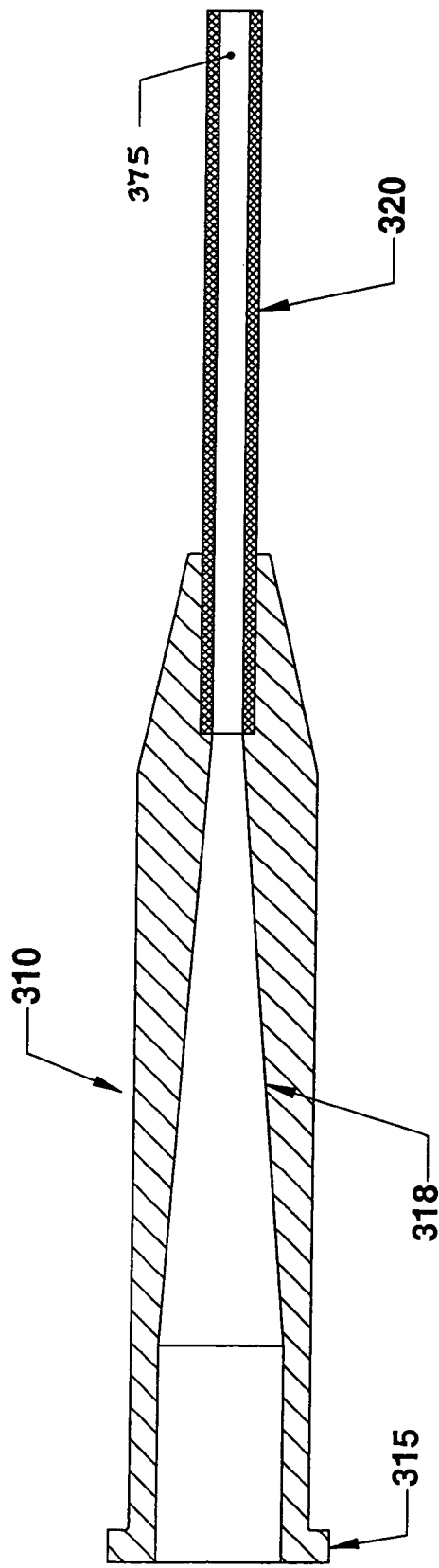
FIG. 3f is a longitudinal cross-section of a proximal hub of a Sheath Catheter, under an embodiment.

FIG. 3f is a longitudinal cross-section of a proximal hub of a Sheath Catheter 300, under an embodiment. The proximal hub 310 is fabricated using at least one of polycarbonate, nylons and other injection moldable polymers, but is not so limited. The proximal hub 310 may be connected to the Sheath Catheter proximal shaft 320 via one of gluing, insert molding and thermal bonding. The proximal hub 310 has a proximal luer connector for connection to other devices such as syringes (for flushing the catheter with saline before use, for example). The proximal luer also includes a lead-in area 318 that gradually tapers the proximal opening of the luer into the proximal lumen 375 of the Sheath Catheter. The lead-in 318 allows easy introduction of the Sheath Introducer 350 or Blunt Dissection Catheter 100 into the Sheath Catheter 300.

The Sheath Catheter 300 described above includes a uniform inner diameter that has a high tolerance fit to the outer diameter of the Blunt Dissection Catheter 100. The Sheath Catheter of an alternative embodiment includes a distal segment of the Sheath Catheter shaft having a high tolerance fit to the outer diameter of the Blunt Dissection Catheter 100, and proximal to this segment, the inner diameter of the Sheath Catheter may be increased slightly. This configuration provides more annular space between the Blunt Dissection Catheter and the Sheath Catheter to provide improved overall movement of the Blunt Dissection Catheter within the Sheath Catheter.

Lengths of the distal segment having a high tolerance fit to the outer diameter of the Blunt Dissection Catheter 100 have a wide range, wherein the lower limit includes only the distalmost 1 cm of the Sheath Catheter 300, and the upper limit approaches the entire length of the Sheath Catheter 300. A practical range for the distal segment of the Sheath Catheter having a high tolerance fit to the Blunt Dissection Catheter is approximately 5 cm to 20 cm. The increase in diameter may be on the order of 0.002 to 0.015 inches, but is not so limited. As a practical example, the inner diameter of the distal segment of the Sheath Catheter has a nominal diameter of approximately 0.042 inches, and the inner diameter proximal to the distal segment can be increased to 0.045 or 0.047 inches. This small increase in annular space can provide significant improvement in movement. However, in both embodiments described, it is desirable to maintain an intimate, high tolerance fit between the distal segment of the Sheath Catheter and the Blunt Dissection Catheter to provide the low possible profile at the distal end of the integrated system.

Figure 4A:
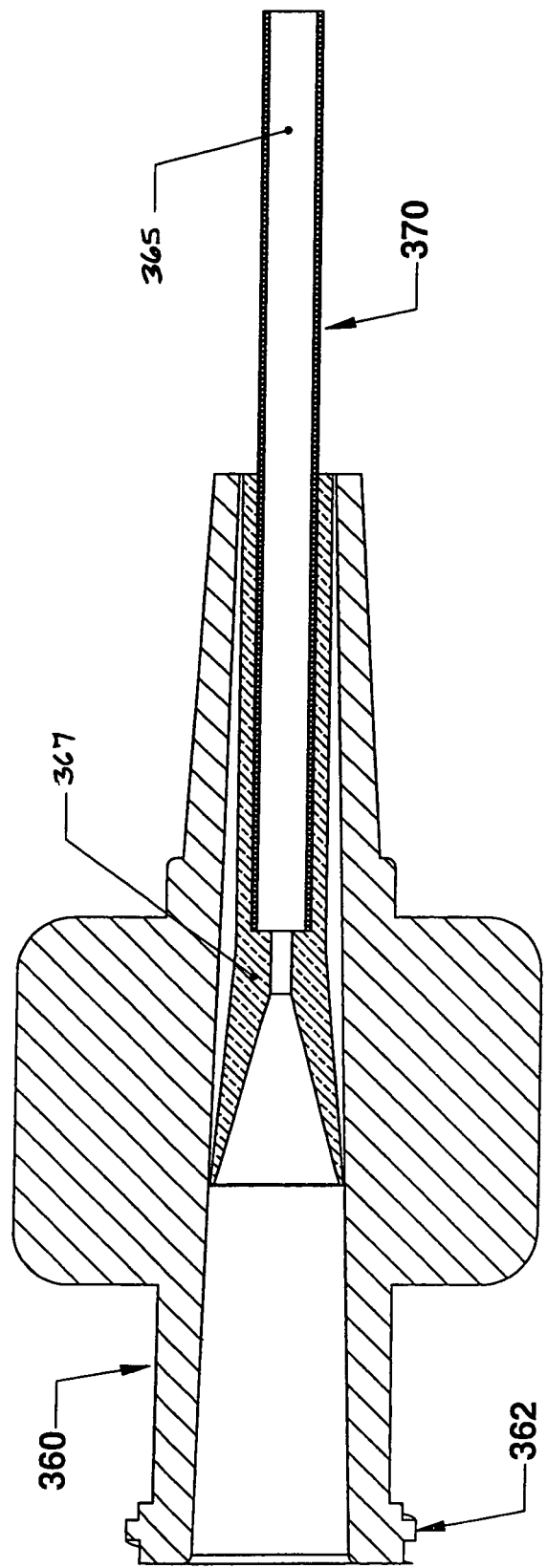
FIG. 4a is a longitudinal cross-section of an Introducer Catheter proximal hub, under an embodiment.

FIG. 4a is a longitudinal cross-section of an Sheath Introducer proximal hub, under an embodiment. FIG. 4b is a longitudinal cross-section of an Sheath Introducer distal segment in a tapered configuration and including a fluoroscopic marker band, under an embodiment. FIG. 4c is a longitudinal cross-section of an Sheath Introducer distal segment in a rounded configuration and including a fluoroscopic marker band, under an embodiment.

With reference to FIGS. 4a, 4b, and 4c, the Sheath Introducer includes the hub 360, the shaft 370 and the fluoroscopic markerband 385. The Sheath Introducer 350 is configured to be inserted inside the Sheath Catheter 300 such that, with full insertion, the distal segment of the Sheath Introducer shaft 370 extends beyond the distal end of the Sheath Catheter 300 by approximately 0.5 cm to 5 cm, but is not so limited, and the Sheath Introducer proximal hub 360 is press fit into the Sheath Catheters proximal hub 310. The Sheath Introducer shaft 370 outer diameter is configured to provide an intimate fit to the inner diameter of the Sheath Catheter 300, as described above for the fit between the Blunt Dissection Catheter 100 and the Sheath Catheter 300.

As an assembly, the Sheath Introducer/Sheath Catheter can be tracked over a guide wire to the appropriate vascular site via the Sheath Introducers central guide wire lumen 365. As described previously, the Sheath Catheter 300 generally may not be tracked on its own over a guide wire, since the inner diameter of the Sheath Catheter 300 has a nominal diameter of approximately 0.042 inches and a conventional coronary guide wire has a diameter of approximately 0.014 inches. Thus a large annular gap would exist, exposing the leading edge of the Sheath Catheter against the vessel wall. The Sheath Introducer provides the physical interface between the guide wire and Sheath Catheter 300, filling the annual gap between the two catheters.

The Sheath Introducer shaft 370 of an embodiment includes lubricious materials that improve tracking over the guide wire, and ease the retraction of the Sheath Introducer 350 from the Sheath Catheter 300 once the system has been advanced to the appropriate vascular site. Suitable lubricious materials include polytetrafluoroethylene (PTFE), high density polyethylene (HDPE) or low density polyethylene (LDPE). Typical dimensions of the Sheath Introducer shaft include an inner diameter of approximately 0.016 to 0.022 inches, and an outer diameter of approximately 0.039 to 0.043 inches, but the embodiment is not limited to these dimensions. Upon full insertion of the Sheath Introducer 350 into the Sheath Catheter 300, a pre-determined distal segment of the Sheath Introducer shaft 370 extends beyond the distal end of the Sheath Catheter 300 as described above. This length allows a smooth transition from the Sheath Introducer 350 to the Sheath Catheter 300 and facilitates tracking over the guide wire.

The proximal hub 360 is shown connected to the Sheath Introducer shaft 370, with reference to FIG. 4a. The proximal hub 360 is formed using at least one of polycarbonate, nylon and other suitable injection moldable polymers. The proximal hub 360 includes a proximal luer fitting 362 used to connect to conventional devices such as a syringe used to flush the lumen 365 with saline prior to usage. The proximal hub 360 also includes a guide wire lead-in 367 that provides a smooth transition from the proximal opening of the hub 360 to the proximal lumen of the shaft 370, and allows the easy advancement of the guide wire into the Sheath Introducer 350. The guide wire lead-in 367 may also be formed using at least one of polycarbonate, nylon and other suitable injection moldable polymers. The proximal hub 360, guide wire lead-in 367 and shaft 370 are connected using one of a combination of gluing, insert molding and thermal bonding. Alternatively, the guide wire lead-in 367 and the proximal hub form a one-piece component.

Referring to FIGS. 4b and 4c, the distal end of the Sheath Introducer shaft 370 includes a fluoroscopic marker band 385. The marker band is imbedded in or coupled to the wall of the Sheath Introducer shaft 370 via several embodiments. In a first embodiment, as shown in FIGS. 4b and 4c, the marker band 485 is swaged into the body of the Sheath Introducer shaft 370 such that the external surface of the marker band 385 is flush with the outer surface of the Sheath Introducer shaft 370. This provides an adequate physical lock of the marker band within the Sheath Introducer shaft 370, requiring minimal overall thickness of the Sheath Introducer shaft 370. A nominal polymer thickness that covers the marker band is on the order of approximately 0.002 to 0.004 inches, but is not so limited.

In a second embodiment the interior surface of the marker band 385 and the interior surface of the Sheath Introducer shaft 370 are flush. This embodiment uses an equal thickness of Sheath Introducer shaft 370. In a third embodiment, the marker band 385 is completely contained within the body of the Sheath Introducer shaft 370, and a thin layer of polymer covers both the inside surface and outside surface of the marker band 385. The thickness of this layer ranges from approximately 0.001 to 0.003 inches, but is not so limited.

The distal end of the Sheath Introducer can terminate in a tapered shape or a rounded shape. The shape of the tip is heat-formed in a manner similar to that described for the distal termination of the Sheath Catheter 300. These shapes provide a smooth transition for the guide wire to the Sheath Introducer distal end, and assist in tracking the distal end of the Sheath Introducer over a guide wire, especially in tight heavily diseased vessels.

Figure 5A:
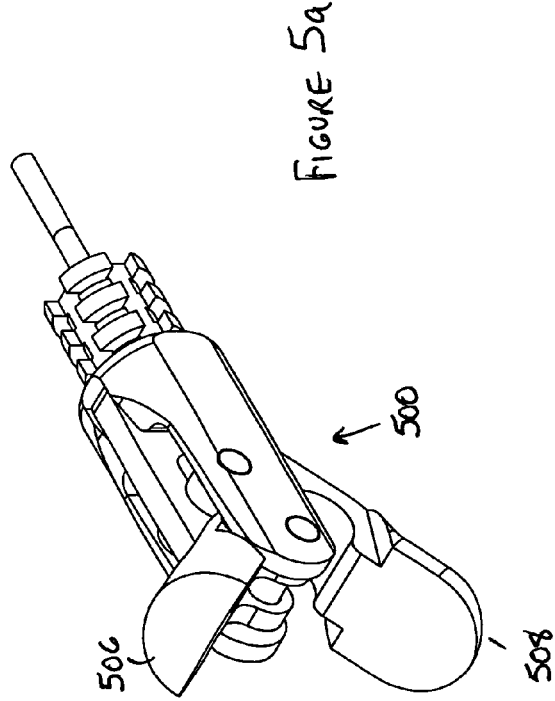
FIG. 5a is a working element of a Blunt Dissection Catheter showing two spreading members in an open configuration, under an embodiment.
Figure 5B:
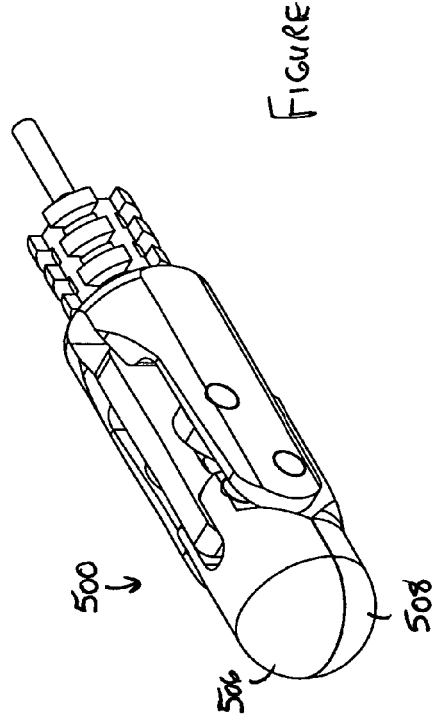
FIG. 5b is a working element of a Blunt Dissection Catheter showing two spreading members in a closed configuration, under an embodiment.
Figure 5C:
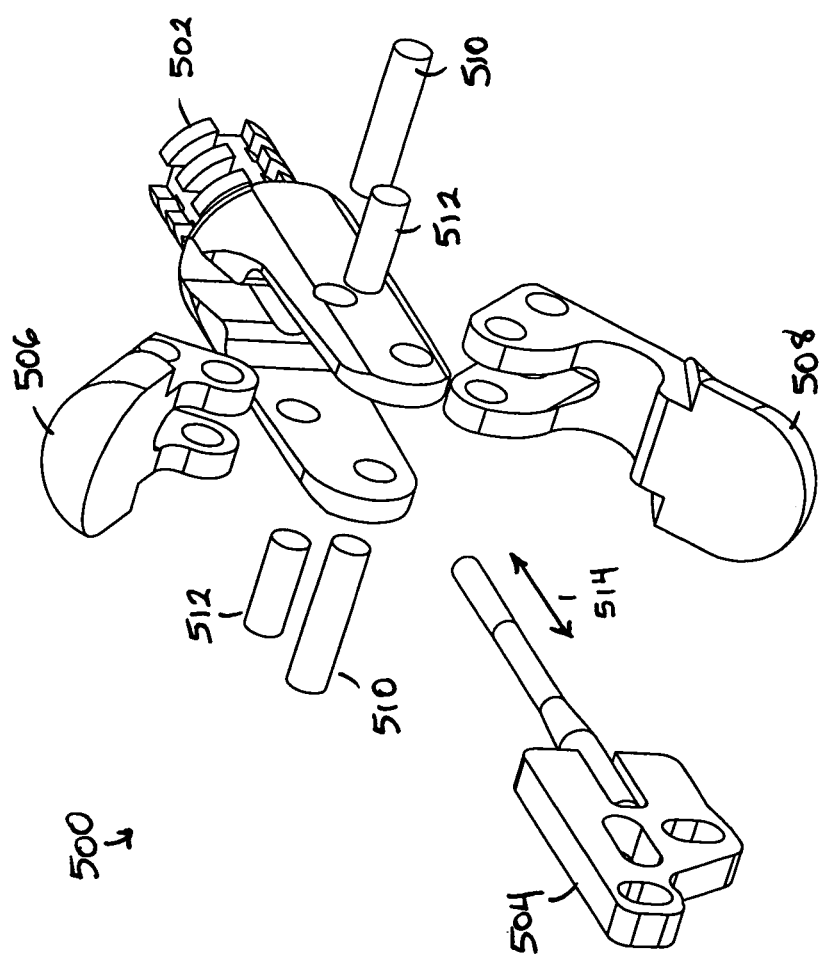
FIG. 5c is an exploded view of a working element of a Blunt Dissection Catheter, under an embodiment.

The Blunt Dissection Catheter described above can be any of a number of catheters and/or working elements. As examples, complete descriptions of representative Blunt Dissection Catheters are found in U.S. Pat. Nos. 5,968,064, 6,508,825, 6,599,304, and 6,638,247, as well as United States Patent Application Publication number US-2004-0077999-A1 and U.S. patent application Ser. No. 09/835,043. FIG. 5a is a working element 500 of a Blunt Dissection Catheter showing two spreading members 506/508 in an open configuration, under an embodiment. The working element 500 is but one example of working element 120 described above with reference to FIG. 1 and the sequence of FIGS. 2a-2i and the embodiment is not so limited. FIG. 5b is a working element 500 of a Blunt Dissection Catheter showing two spreading members 506/508 in a closed configuration, under an embodiment. FIG. 5c is an exploded view of a working element 500 of a Blunt Dissection Catheter, under an embodiment.

Referring to FIG. 5c, the working element 500 includes a base section 502, an actuation assembly 504, a first spreading member 506, and a second spreading member 508. The hinge pins 510 couple the first 506 and second 508 spreading members to the actuation assembly 504 and the base section 502. The hinge pins 510 support rotation of a distal end of each of the first 506 and second 508 spreading members around a proximal end of the spreading members 506/508 during deployment of the spreading members 506/508 as described above. The clevis pins 512 couple the actuation assembly 504 to each of the spreading members 506/508. Consequently, the coupling between the actuation assembly 504, the hinge pins 510, the clevis pins 512, and the spreading members 506/508 allows for the conversion of a linear actuation force 514 applied to the actuation assembly 504 into the radial motion of the respective spreading members around the respective hinge pins 510.

In operations as described above, the working element 500 is placed into contact or approximate contact with a vascular occlusion and/or blood vessel wall to facilitate the disruption of the vascular occlusion. An actuation force 514, including one exerted linearly in a proximal direction, is applied to the actuation assembly 504, converted into a spreading or mechanical force and motion (e.g., outward radial force and motion with respect to the spreading members 506/508 respective hinge pin 510) and then exerted by the spreading members 506/508 on the vascular walls. The spreading or mechanical force applied to the vascular occlusion and/or a blood vessel wall tears, fractures or otherwise disrupts, a vascular occlusion without damaging the surrounding blood vessel wall. As described above, the continued linear disruption of the vascular occlusion generates a channel or passageway of sufficient size for the passage of the working element 500 and the catheter system to cross the occlusion. A guide wire or other catheter known in the art can then be advanced within the dissected occlusion for elective medical procedures.

Unless the context clearly requires otherwise, throughout the description and the claims, the words "comprise," "comprising," and the like are to be construed in an inclusive sense as opposed to an exclusive or exhaustive sense; that is to say, in a sense of "including, but not limited to." Words using the singular or plural number also include the plural or singular number respectively. Additionally, the terms "herein," "hereunder," "above," "below," and terms of similar import, when used in this application, refer to this application as a whole and not to any particular portion of this application. When the word "or" is used in reference to a list of two or more items, that word covers all of the following interpretations of the word: any of the items in the list, all of the items in the list and any combination of the items in the list.

The above description of illustrated embodiments of the catheter system is not intended to be exhaustive or to limit the catheter system to the precise form disclosed. While specific embodiments of, and examples for, the catheter system are described herein for illustrative purposes, various equivalent modifications are possible within the scope of the catheter system, as those skilled in the relevant art will recognize. The teachings of the catheter system provided herein can be applied to other medical devices and systems, not only for the catheter systems described above.

The elements and acts of the various embodiments described above can be combined to provide further embodiments of the catheter system. These and other changes can be made to the catheter system in view of the above detailed description.

All of the above references and United States patents and patent applications are incorporated herein by reference. Aspects of the catheter system can be modified, if necessary, to employ the systems, functions and concepts of the various patents and applications described above to provide yet further embodiments of the system.

In general, in the following claims, the terms used should not be construed to limit the catheter system to the specific embodiments disclosed in the specification and the claims, but should be construed to include all catheter systems and medical devices that operate under the claims to cross vascular occlusions. Accordingly, the catheter system is not limited by the disclosure, but instead the scope of the catheter system is to be determined entirely by the claims.

While certain aspects of the catheter system are presented below in certain claim forms, the inventors contemplate the various aspects of the catheter system in any number of claim forms. Accordingly, the inventors reserve the right to add additional claims after filing the application to pursue such additional claim forms for other aspects of the catheter system.

What is claimed is:

1. A catheter system comprising:
   a catheter shaft including a braided tubular member having an inner surface and an outer surface, the braided tubular member comprising braided filaments formed into a mesh; at least one inner polymer layer having an inner surface and an outer surface and formed from a lubricious polymer coupled to the inner surface of the braided tubular member, the outer surface of the at least one inner polymer layer being configured with microscopic interstices; at least one outer polymer laminate layer coupled to the outer surface of the braided tubular member, wherein the polymer materials of the outer polymer laminate layer are interspersed through the braided tubular member and connect into interstices of the outer surface of the inner polymer layer, the thickness of the outer polymer laminate layer being configured to cover the braided tubular member thereby forming a smooth uninterrupted surface; at least one lumen in the catheter shaft, wherein the inner polymer layer and the outer polymer laminate layer are bonded together between cross-over points of the braided structure and form bridges that connect into the microscopic interstices of the inner polymeric layer thereby forming a unified structure; and
   a sheath introducer including a member having a proximal and a distal end and forming a single lumen configured to track over a guide wire, wherein the member is configured to be inserted into the catheter shaft, wherein a distal region of the member extends beyond a distal end of the catheter shaft when the member is fully inserted.

2. The system of claim 1, wherein the sheath introducer further comprises at least one hub on the proximal end, the hub configured to lock into a hub on a proximal end of the catheter shaft when the sheath introducer is fully inserted into the catheter shaft.

3. The system of claim 1, wherein the sheath introducer further comprises a fluoroscopic marker system in a distal region of the member.

* * * * *

UNITED STATES PATENT AND TRADEMARK OFFICE
CERTIFICATE OF CORRECTION

| | | |
|---|---|---|
| PATENT NO. | : 8,702,679 B2 | Page 1 of 1 |
| APPLICATION NO. | : 10/865231 | |
| DATED | : April 22, 2014 | |
| INVENTOR(S) | : Deckman et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1955 days.

Signed and Sealed this
Twenty-first Day of July, 2015

Michelle K. Lee
*Director of the United States Patent and Trademark Office*